United States Patent [19]

Carceller et al.

[11] Patent Number: 5,747,477
[45] Date of Patent: May 5, 1998

[54] AZO DERIVATIVES OF 5-AMINOSALICYLIC ACID

[75] Inventors: Elena Carceller, Sant Cugat; Pere J. Jimenez, Flix; Jordi Salas, Montornes del Valles; Carmen Almansa, Barcelona; Javier Bartroli, Barcelona; Manel Merlos, Barcelona; Marta Giral, Barcelona; Dolors Balsa, Badalona; Rosa Ferrando, Barcelona; Julian Garcia-Rafanell, Barcelona; Javier Forn, Barcelona, all of Spain

[73] Assignee: J. Uriach & Cia S.A., Barcelona, Spain

[21] Appl. No.: 836,125
[22] PCT Filed: Sep. 6, 1996
[86] PCT No.: PCT/EP96/03921
  § 371 Date: May 8, 1997
  § 102(e) Date: May 8, 1997
[87] PCT Pub. No.: WO97/09329
  PCT Pub. Date: Mar. 13, 1997

[30] Foreign Application Priority Data

Sep. 8, 1995 [ES] Spain ................. 95 01752
Oct. 11, 1995 [ES] Spain ................. 95 01967

[51] Int. Cl.$^6$ .............. A61K 31/655; C07D 471/04
[52] U.S. Cl. ........................... 514/150; 534/664
[58] Field of Search .................... 534/664; 514/150

[56] References Cited

U.S. PATENT DOCUMENTS

| 2,396,145 | 3/1946 | Anders et al. ............ 534/664 |
| 4,312,806 | 1/1982 | Lambert et al. ........... 534/664 |
| 5,516,783 | 5/1996 | Whittaker et al. ......... 514/303 |

FOREIGN PATENT DOCUMENTS

| 92/03423 | 3/1992 | WIPO. |
| 96/14317 | 5/1996 | WIPO. |

*Primary Examiner*—Fiona T. Powers
*Attorney, Agent, or Firm*—Burns, Doane, Swecker & Mathis, L.L.P.

[57] ABSTRACT

Compounds of formula I and their salts and solvates are useful for the treatment or prevention of inflammatory bowel disease. Pharmaceutical compositions including these compounds and processes for their preparation are also provided.

16 Claims, 1 Drawing Sheet

AZO DERIVATIVES OF 5-AMINOSALICYLIC ACID

This application is a 371 of PCT/EP96/03921 filed Sep. 6, 1996.

FIELD OF THE INVENTION

The present invention relates to new azo derivatives of 5-aminosalicylic acid, to pharmaceutical compositions containing these compounds, to a process for their preparation and to their use in the treatment or prevention of inflammatory bowel disease.

DESCRIPTION OF THE PRIOR ART

Inflammatory bowel disease (IBD) is a general term for a group of chronic inflammatory disorders of unknown etiology involving the gastrointestinal tract. IBD may be divided into two major groups, ulcerative colitis and Crohn's disease. Both of them are of a recurrent nature, characterized by periodic outbreaks and remissions. Relapses occur even after surgery and therefore this option is reserved for specific complications or intractability of the disease.

Sulfasalazine, although originally developed in the 1940's for the treatment of rheumatoid arthritis, is now one of the most widely prescribed drugs for inflammatory bowel disease. Sulfasalazine consists of a salicylate (5-aminosalicylate) linked to sulfapyridine by an azo bond. It has been demonstrated that sulfasalazine is split by the colonic bacteria, releasing 5-aminosalicylic acid (5-ASA), and sulfapyridine. Sulfapyridine is almost completely absorbed from the colon, metabolised and excreted in the urine, while 5-ASA is poorly absorbed from the colon. Most of the side effects of sulfasalazine have been ascribed to the sulfapyridine moiety (Das et al., New Engl. J. Med. 1973; 289:491–495). In 1977 Azad Khan et al. demonstrated that in ulcerative colitis the active moiety is 5-ASA (Azad Khan, A.K. et al., Lancet 1977; 2: 892–5) and that sulfapyridine acts only as a carrier and favouring the liberation of 5-ASA in the colon. After this discovery, several new 5-ASA based drugs have been developed, such as slow- or delayed-release formulations of plain 5-ASA or other azo compounds (e. g. Olsalazine, Balsalazine, Ipsalazide). However, no drug is presently available which is able to produce a complete remission of the symptoms and prevent subsequent relapses.

Recently, it has been suggested that PAF could play a key role in the pathogenesis of ulcerative colitis, since elevated levels of this substance have been detected in samples of colonic tissue from patients with this disorder (Wengrower et al., Gastroenterology, 1987; 92) and it has been shown that intravenous administration of PAF induces colitis (Gonzalez-Crusi et al., Am. J. Pathol. 1983; 112:127–35 and Hseuh et al. Am. J. Pathol. 1986; 122:231–9) and gastritis (Rosam et al., Nature 1986; 319:54–6 and Wallace et al., Prostaglandins 1986; 31:989–98).

The present invention discloses a series of compounds containing the 4-hydroxy-3-carboxyphenylazo moiety which can be metabolised in the colon in a similar manner to sulfasalazine, delivering 5-ASA and an aromatic amine having PAF antagonist activity. With the compounds of the present invention not only it is possible to avoid the side effects of sulfapyridine, but also, by using. a PAF antagonist as the carrier of 5-ASA, they may be more effective in the therapy of inflammatory bowel disease than current treatments. Such an approach is totally new since never before compounds combining in the same molecule a PAF antagonist and 5-aminosalicylic acid have been described in the literature.

DESCRIPTION OF THE INVENTION

The present invention relates to new azo derivatives of 5-aminosalicylic acid of general formula I:

wherein:
the 4-hydroxy-3-carboxyphenylazo moiety can be at the 3- or 4-position of the benzene ring;
m represents 1 or 2;
$R^1$ represents $C_{1-4}$ alkyl or $C_{3-7}$ cycloalkyl;
a, b and c represent $CR^2$, wherein each $R^2$ independently represents hydrogen or $C_{1-4}$ alkyl;
X represents a group of formula (i) or (ii):

wherein these groups are bound to the phenyl ring in formula I via B and Z, respectively;
A represents —CO—, —SO$_2$—, —NHCO— or —OCO—;
B represents a group of formula (iii), and when A represents —CO— or —SO$_2$—, B can also represent a group of formula (iv), (v), (vi) or (vii);

n represents 0, 1, 2 or 3;
p represents 0 or 1;
$R^3$ represents hydrogen, $C_{1-4}$ alkyl, $C_{1-4}$ haloalkyl, $C_{3-7}$ cycloalkyl, $C_{1-4}$ alkoxy-$C_{1-4}$ alkyl or aryl;
$R^4$ represents hydrogen, $C_{1-4}$ alkyl, —COOR$^5$ or —CONR$^5$R$^6$, and when A represents —CO— or —SO$_2$—, then $R^4$ can also represent —NR$^5$R$^6$, —NR$^7$C(=O)OR$^5$, —NR$^7$C(=O)R$^5$, —NR$^7$C(=O)NR$^5$R$^6$ or —NR$^7$SO$_2$R$^5$;

or $R^3$ and $R^4$ together form a $C_{2-6}$ polymethylene chain;
$R^5$ represents $C_{1-4}$ alkyl, aryl or aryl-$C_{1-4}$ alkyl;
$R^6$ and $R^7$ independently represent hydrogen or $C_{1-4}$ alkyl;
W represents —OC(=O)—, —C(=O)—, —NR$^6$C(=O)— or —SO$_2$—;
$R^8$ represents aryl;
$R^9$ represents $C_{1-4}$ alkyl, $C_{3-7}$ cycloalkyl, —C(=O)OR$^5$, —C(=O)R$^5$, —C(=O)NR$^5$R$^6$, or —SO$_2$R$^5$;
$R^{10}$ represents $C_{1-4}$ alkyl, $C_{3-7}$ cycloalkyl, aryl, or aryl-$C_{1-4}$alkyl;
Z represents —(CH$_2$)$_q$CO— or —(CH$_2$)$_r$—;
q represents 0, 1 or 2;
r represents 1 or 2;
$R^{11}$ represents hydrogen or halogen;
$R^{12}$ and $R^{13}$ independently represent hydrogen, $C_{1-6}$ alkyl, $C_{3-7}$ cycloalkyl or $C_{3-7}$ cycloalkyl-$C_{1-6}$ alkyl;
or $R^{12}$ and $R^{13}$ together form a $C_{2-6}$ polymethylene chain;
$R^{14}$ represents —COR$^{15}$, —COOH, —COOR$^{15}$, —CONR$^{16}$R$^{17}$, —C$_{1-6}$ alkyl—OR$^{15}$, —C$_{1-6}$ alkyl—OC(=O)R$^{15}$ or —C$_{1-6}$ alkyl—OC(=O)NR$^{16}$R$^{17}$;
$R^{15}$ represents $C_{1-6}$ alkyl, $C_{2-6}$ alkenyl, $C_{2-6}$ alkynyl, $C_{3-7}$ cycloalkyl or $C_{1-6}$ haloalkyl;
$R^{16}$ and $R^{17}$ independently represent hydrogen or any of the meanings disclosed for $R^{15}$;
aryl, whenever appearing in the above definitions, represents phenyl or phenyl substituted with 1, 2, 3 or 4 groups independently selected from halogen, $C_{1-4}$ alkyl, $C_{1-4}$ alkoxy, hydroxy, $C_{1-4}$ haloalkyl, $C_{1-4}$ haloalkoxy, $C_{1-4}$ alkylcarbonyl, $C_{1-4}$ alkylcarbonyloxy, $C_{1-4}$ alkoxycarbonyl, $C_{1-4}$ alkylsulfonyl, $C_{1-4}$ alkylsulfinyl, $C_{1-4}$ alkylthio, or $C_{1-4}$ alkylcarbonylamino;
and the salts and solvates thereof.

The invention also provides a pharmaceutical composition which comprises an effective amount of a compound of formula I or a pharmaceutically acceptable salt or solvate thereof in admixture with one or more pharmaceutically acceptable excipients.

The invention further provides the use of a compound of formula I or a pharmaceutically acceptable salt or solvate thereof for the manufacture of a medicament for the treatment or prevention of inflammatory bowel disease in animals, including human beings.

The invention further provides the use of a compound of formula I or a pharmaceutically acceptable salt or solvate thereof for the treatment or prevention of inflammatory bowel disease in animals, including human beings.

The invention also provides a method of treating or preventing inflammatory bowel disease in animals, including human beings, which method comprises administering to a patient in need thereof an effective amount of a compound of formula I or a pharmaceutically acceptable salt or solvate thereof.

The invention also provides a process for preparing a compound of formula I, which comprises:
(a) converting an amine of formula II

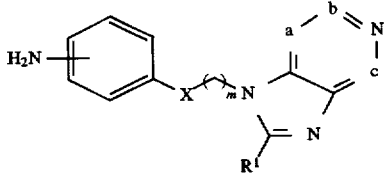

wherein the amino group can be at the 3- or 4-position of the benzene ring and a, b, c, m, $R^1$ and X are as defined above, into the corresponding diazonium salt, and then allowing this to react with salicylic acid; or (b) reacting an amine of formula II with 5-nitrososalicylic acid; or
(c) reacting a nitroso derivative of formula

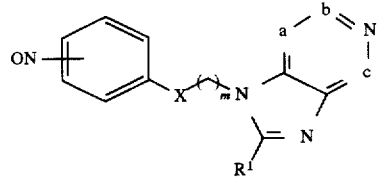

wherein the NO group can be at the 3- or 4-position of the benzene ring and a, b, c, m, $R^1$ and X are as defined above, with 5-aminosalicylic acid; and
(d) if desired, after steps (a), (b) or (c), reacting a compound of formula I with an acid or a base to give the corresponding salt.

The compounds of formula I can have one or more asymmetric centers, which can give rise to stereoisomers. The present invention relates to each of the individual stereoisomers as well as to the mixtures thereof. Moreover, some of the compounds of the present invention may show cis/trans isomery. The present invention covers each of the geometric isomers and the mixtures thereof.

In the above definitions, the term $C_{1-n}$ alkyl, as a group or part of a group, means a linear or branched alkyl group that contains from one to n carbon atoms. Therefore, when n is 4 it includes methyl, ethyl, propyl, isopropyl, butyl, isobutyl, sec-butyl, and tert-butyl. When n is 6 it includes, among others, methyl, ethyl, propyl, isopropyl, butyl, isobutyl, sec-butyl, tert-butyl, pentyl, neopentyl and hexyl.

A $C_{2-6}$ alkenyl group means linear or branched alkyl group having from 2 to 6 carbon atoms and having in addition one or more double bonds.

Examples include vinyl, 1- and 2-propenyl, 1-, 2- and 3-butenyl, 2-methyl-2-propenyl, 1-, 2-, 3- and 4-pentenyl, and 1-, 2-, 3-, 4- and 5-hexenyl.

A $C_{2-6}$ alkynyl group means linear or branched alkyl group having from 2 to 6 carbon atoms and having in addition one or more triple bonds. Examples include among others ethynyl, 1- and 2-propynyl, 1-, 2- and 3-butynyl, 1-, 2-, 3- and 4-pentynyl, 1-, 2-, 3-, 4- and 5-hexynyl.

The term halogen or its abbreviation halo means fluoro, chloro, bromo or iodo.

A $C_{3-7}$ cycloalkyl group, as a group or part of a group, represents cyclopropyl, cyclobutyl, cyclopentyl, cyclohexyl or cycloheptyl.

A $C_{2-6}$ polymethylene chain represents ethylene, propylene, butylene, pentylene or hexylene.

The term $C_{1-4}$ alkoxy, as a group or part of a group, means a group derived from the union of a $C_{1-4}$ alkyl group like the above mentioned to an oxygen atom of an ether functional group. Examples include methoxy, ethoxy, propoxy, isopropoxy, butoxy, isobutoxy, sec-butoxy, and tert-butoxy.

The term $C_{1-n}$ haloalkyl means a group resulting from the substitution of one or more hydrogen atoms of a $C_{1-n}$ alkyl group by one or more halogen atoms (i.e. fluorine, chlorine, bromine or iodine), which can be the same or different. When n is 4, examples include trifluoromethyl, fluoromethyl, chloromethyl, bromomethyl, iodomethyl, 1- and 2-chloroethyl, 1- and 2-fluoroethyl, 1- and 2-iodoethyl, 2,2,2-trifluoroethyl, 2,2,2-trichloroethyl, pentafluoroethyl, 1-, 2- and 3-fluoropropyl, 1-, 2- and 3-chloropropyl, 3,3,3-trifluoropropyl, 2,2,3,3,3-pentafluoropropyl, heptafluoropropyl, 1-, 2-, 3- and 4-fluorobutyl, 1-, 2-, 3- and 4-chlorobutyl, and nonafluorobutyl. When n is 6, examples include trifluoromethyl, fluoromethyl, chloromethyl, bromomethyl, iodomethyl, 1- and 2-chloroethyl, 1- and 2-fluoroethyl, 1- and 2-iodoethyl, 2,2,2-trifluoroethyl, 2,2,2-trichloroethyl, pentafluoroethyl, 1-, 2- and 3-fluoropropyl, 1-, 2- and 3-chloropropyl, 3,3,3-trifluoropropyl, 2,2,3,3,3-pentafluoropropyl, heptafluoropropyl, 1-, 2-, 3- and 4-fluorobutyl, 1-, 2-, 3- and 4-chlorobutyl, nonafluorobutyl, 1-, 2-, 3-, 4- and 5-fluoropentyl, 1-, 2-, 3-, 4- and 5-chloropentyl, 1-, 2-, 3-, 4-, 5- and 6-fluorohexyl, and 1-, 2-, 3-, 4-, 5- and 6-chlorohexyl.

A $C_{1-4}$ haloalkoxy group means a group resulting from the substitution of one or more hydrogen atoms of a $C_{1-4}$ alkoxy group by one or more halogen atoms, which can be the same or different. Examples include trifluoromethoxy, fluoromethoxy, chloroethoxy, fluoroethoxy, iodoethoxy, 2,2,2-trifluoroethoxy pentafluoroethoxy, fluoropropoxy, chloropropoxy, 2,2,3,3,3-pentafluoropropoxy, heptafluoropropoxy, fluorobutoxy, and nonafluorobutoxy.

A $C_{1-4}$ alkylcarbonyl group represents a group resulting from the union of a $C_{1-4}$ alkyl group to a carbonyl group. Examples include acetyl, propionyl, isopropionyl, and butanoyl.

A $C_{1-4}$ alkylcarbonyloxy group represents a group resulting from the union of a $C_{1-4}$ alkylcarbonyl group to an oxygen atom of an ether functional group. Examples include acetyloxy, propionyloxy, isopropionyloxy, and butanoyloxy.

A $C_{1-4}$ alkoxycarbonyl group represents a group resulting from the union of a $C_{1-4}$ alkoxy group to a carbonyl group. Examples include methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl.

A $C_{1-4}$ alkylsulfonyl group represents a group resulting from the union of a $C_{1-4}$ alkyl group to a sulfonyl group. Examples include methylsulfonyl, ethylsulfonyl, propylsulfonyl, isopropylsulfonyl, butylsulfonyl, isobutylsulfonyl, sec-butylsulfonyl, and tert-butylsulfonyl.

A $C_{1-4}$ alkylsulfinyl group represents a group resulting from the union of a $C_{1-4}$ alkyl group to a sulfinyl group. Examples include methylsulfinyl, ethylsulfinyl, propylsulfinyl, isopropylsulfinyl, butylsulfinyl, isobutylsulfinyl, sec-butylsulfinyl, and tert-butylsulfinyl.

A $C_{1-4}$ alkylthio group represents a group resulting from the union of a $C_{1-4}$ alkyl group to a sulphur atom of a thioether funtional group. Examples include methylthio, ethylthio, propylthio, isopropylthio, butylthio, isobutylthio, sec-butylthio, and tert-butylthio.

A $C_{1-4}$ alkylcarbonylamino group represents a group resulting from the substitution of a hydrogen atom of an amino group by a $C_{1-4}$ alkylcarbonyl group. Examples include acetamido, propanamido and isopropanamido.

A $C_{1-4}$ alkoxy$C_{1-4}$ alkyl group represents a group resulting from the substitution of a hydrogen atom of a $C_{1-4}$ alkyl group by a $C_{1-4}$ alkoxv group. Examples include among others methoxymethyl, ethoxymethyl, propoxymethyl, isopropoxymethyl, butoxymethyl, isobutoxymethyl, sec-butoxymethyl, tert-butoxymethyl, 2-methoxyethyl, 2-ethoxyethyl, 2-propoxyethyl, 2-isopropoxyethyl, 2-butoxyethyl, 2-isobutoxyethyl, 2-sec-butoxyethyl, 2-tert-butoxyethyl, 1-methoxyethyl, 1-ethoxyethyl, 1-propoxyethyl, 1-isopropoxyethyl, 1-butoxyethyl, 1-isobutoxyethyl, 1-sec-butoxyethyl, and 1-tert-butoxyethyl.

An aryl-$C_{1-4}$ alkyl group represents a group resulting from the substitution of one hydrogen atom of a $C_{1-4}$ alkyl group by an aryl group as defined above. Examples include among others, benzyl, 1-phenylethyl, 3-phenylpropyl, 2-phenylpropyl, 1-phenylpropyl, 4-phenylbutyl, 3-phenylbutyl, 2-phenylbutyl and 1-phenylbutyl, wherein the phenyl groups can be substituted as described above in the definition of an aryl group.

In a preferred embodiment of the present invention, X represents a group of formula (i), thus giving rise to compounds represented by formula Ia:

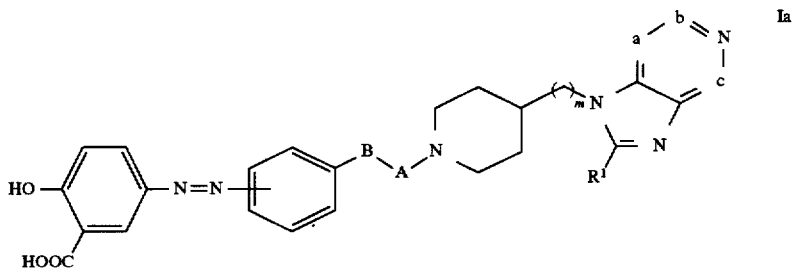

wherein a, b, c, A, B, m and $R^1$ are as defined in general formula I.

Within compounds of formula Ia, those wherein A represents —CO— are preferred. More preferably A represents —CO— and B represents a group of formula (iii), (v) or (vii). Still more preferred are the following groups of compounds of formula Ia:

1) Those wherein A represents —CO—; B represents a group of formula (iii);
and p represents 0;

2) Those wherein A represents —CO—; B represents a group of formula (v); and
$R^3$ represents $C_{1-4}$ alkyl, C1-4 haloalkyl, $C_{3-7}$ cycloalkyl, $C_{1-4}$ alkoxy-$C_{1-4}$ alkyl or aryl; and 3) Those wherein A represents —CO—; and B represents a group of formula (vii).

In another preferred embodiment of the present invention, X represents a group of formula (ii), thus giving rise to compounds represented by formula Ib:

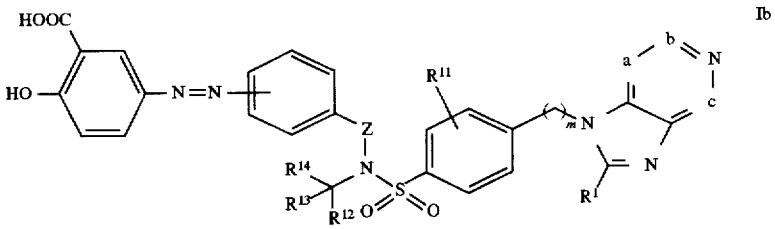

wherein a, b, c, m, R¹, R¹¹, R¹², R¹³, R¹⁴ and Z are as defined in general formula I.

Within compounds of formula Ib, those wherein m represents 1 are preferred. Those compounds of formula Ib wherein m represents 1; $R^{12}$ represents $C_{1-6}$ alkyl, $C_{3-7}$ cycloalkyl or $C_{3-7}$ cycloalkyl-$C_{1-6}$ alkyl; and $R^{13}$ represents hydrogen are more preferred. Still more preferred are those compounds of formula Ib wherein m represents 1; $R^{12}$ represents $C_{1-6}$ alkyl, $C_{3-7}$ cycloalkyl or $C_{3-7}$ cycloalkyl-$C_{1-6}$ alkyl; $R^{13}$ represents hydrogen; and $R^{14}$ represents —$COR^{15}$, —$COOR^{15}$ or —$C_{1-6}$ alkyl—$OR^{15}$. Particularly preferred compounds of formula Ib are those compounds wherein m represents 1; $R^{12}$ represents C1-6 alkyl, C3-7 cycloalkyl or $C_{3-7}$ cycloalkyl-$C_{1-6}$ alkyl; $R^{13}$ represents hydrogen; $R^{14}$ represents —$COR^{15}$, —$COOR^{15}$ or -$C_{1-6}$ alkyl—$OR^{15}$; and $R^{15}$ represents $C_{1-6}$ alkyl.

The compounds of formula I contain basic nitrogen atoms and, consequently, they can form salts with acids, which are also included in the present invention. There is no limitation on the nature of these salts, provided that, when used for therapeutic purposes, they are pharmaceutically acceptable, which, as is well-known in the art, means that they do not have reduced activity or increased toxicity compared with the free compounds. Examples of these salts include: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid, maleic acid, citric acid, succinic acid, tartaric acid; and other mineral and carboxylic acids well known to those skilled in the art.

The compounds of the present invention also contain a carboxy group and, consequently, they can form salts, preferably pharmaceutically acceptable salts. Examples of these salts include salts with inorganic cations such as sodium, potassium, calcium, magnesium, lithium, aluminium, zinc, etc; and salts formed with pharmaceutically acceptable amines such as ammonia, alkylamines, hydroxyalkylamines, lysine, arginine, N-methylglucamine, procaine and the like.

The salts are prepared by reacting the free compound of formula I with a sufficient amount of the desired acid or base to produce a salt in the conventional manner. Free compounds and their salts differ in certain physicochemical properties, such as solubility in polar solvents, but they are equivalent for the purposes of the invention.

The compounds of the present invention can exist in unsolvated as well as solvated forms, including hydrated forms. In general, the solvated forms, with pharmaceutically acceptable solvents such as water, ethanol and the like, are equivalent to the unsolvated forms for the purposes of the invention.

Some compounds of the present invention can exist as different diastereoisomers and/or optical isomers. Diastereoisomers can be separated by conventional techniques such as chromatography or fractional crystallization. The optical isomers can be resolved using any of the conventional techniques of optical resolution to give optically pure isomers. Such a resolution can be performed in any chiral synthetic intermediate as well as in the products of general formula I. Optical resolution techniques include separation by chromatography on a chiral phase or formation of a diastereoisomeric pair, resolution and subsequent recovery of the two enantiomers. The optically pure isomers can also be individually obtained using enantiospecific synthesis. The present invention covers both the individual isomers and their mixtures (e.g. racemic mixtures), whether as obtained by synthesis or by physically mixing them up.

Furthermore, some of the compounds of the present invention may exhibit cis/trans isomery. Geometric isomers can be separated by conventional techniques such as chromatography or recrystallization. Such a separation can be performed either upon the products of formula I or upon any synthetic intermediate thereof. The individual isomers can also be obtained using stereospecific synthesis. The present invention covers each of the geometric isomers and the mixtures thereof.

The present invention also provides processes for preparing the compounds of formula I. In general, they can be obtained using the process shown in the following scheme:

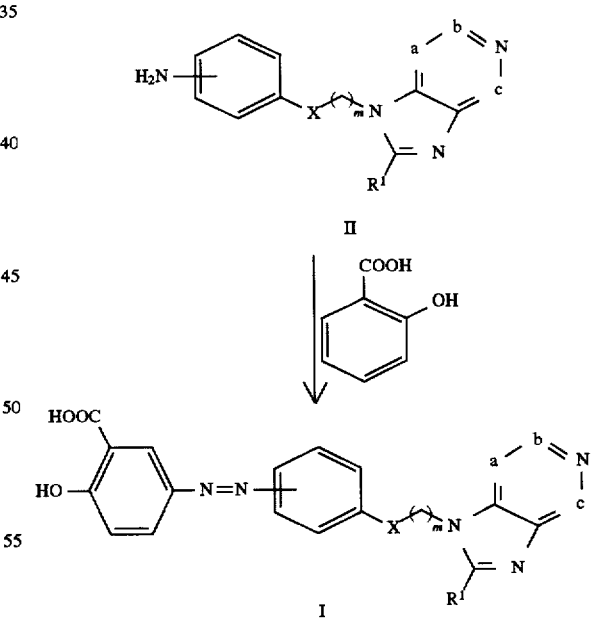

wherein:

the 4-hydroxy-3-carboxyphenylazo moiety can be at the 3- or 4-position of the benzene ring;

the amino group can be at the 3- or 4-position of the benzene ring; and a, b, c, m, $R^1$ and X are as defined above.

Compounds of formula I can be prepared from compounds of formula II by a sequence which involves, as a first step, the conversion of II into the corresponding diazonium salt by treatment for example with nitrous acid or with sodium nitrite in the presence of hydrochloric acid in a suitable solvent such as water or water/acetic acid mixtures, at a temperature preferably comprised between −15° C. and +5° C. and during a reaction time preferably between 30 min and 2 h. Finally, the diazonium salt is treated with salicylic acid under the usual conditions employed in organic synthesis for the preparation of azo bonds, to give a compound of formula I. In general, the reaction is carried out under slightly alkaline conditions, at a temperature preferably comprised between 0° C. and room temperature and during a reaction time preferably comprised between 30 min and 12 h.

Alternatively, compounds of formula I can be prepared using other methods described in the literature for preparing azo bonds, for example by coupling of an amine with a nitroso compound under the reported conditions, which in general involve heating the reactants in a suitable solvent such as acetic acid. Such a condensation can be carried out either by reacting 5-nitrososalicylic acid with a compound of formula II, or by reacting 5-aminosalicylic acid with a nitroso derivative of a compound of formula II (that is, a compound analogous to II but having a NO group in place of the $NH_2$ group). The nitrosoderivatives of II can be prepared using standard procedures, for example by partial oxidation of the amino group of II or by partial reduction of the corresponding nitro derivative (that is, a compound of formula III), which is precisely the precursor of the compounds of formula II, as explained below.

Amines of formula II can be prepared using the procedures described below. As it will be apparent to those skilled in the art, the precise method used for preparing a given compound of formula II may vary depending on its chemical structure.

In general, compounds of formula II can be prepared by reduction of the nitro group present in a compound of formula III, as shown in the following scheme:

wherein:

the nitro and amino groups can be at the 3- or 4-position of the benzene ring; and a, b, c, m, $R^1$ and X are as defined above.

This reduction can be carried out by using any known reducing agent for aromatic nitro groups which is compatible with the other functional groups present in the molecule. Examples of suitable reducing agents include: Zn under a wide range of pH conditions in a suitable solvent such as ethanol-water mixtures at a temperature preferably between room temperature and that of the boiling point of the solvent, more preferably between 50° and 60° C.; $Na_2S_2O_4$ in a suitable solvent such as mixtures of water and an organic solvent, for example tetrahydrofuran, ethanol or pyridine; $SnCl_2$ under a wide range of pH conditions in a suitable organic solvent such as mixtures of water and an alcohol, for example ethanol; Sn or Fe under a wide range of pH conditions; $NaBH_4$ in the presence of a suitable catalyst such as a Sn, Co or Pd salt in a suitable organic solvent such as ethanol; and formic acid or ammonium formate in the presence of Pd/C. Alternatively, the reduction can be carried out by hydrogenation in the presence of a catalyst such as palladium on carbon in a suitable solvent such as an alcohol at a temperature preferably between room temperature and that of the boiling point of the solvent, at a pressure preferably between atmospheric pressure and 10 atmospheres and during a reaction time preferably between 1 and 48 h.

Nitro compounds of formula III can be prepared by some of the processes explained below and summarized in schemes 1, 2 and 3:

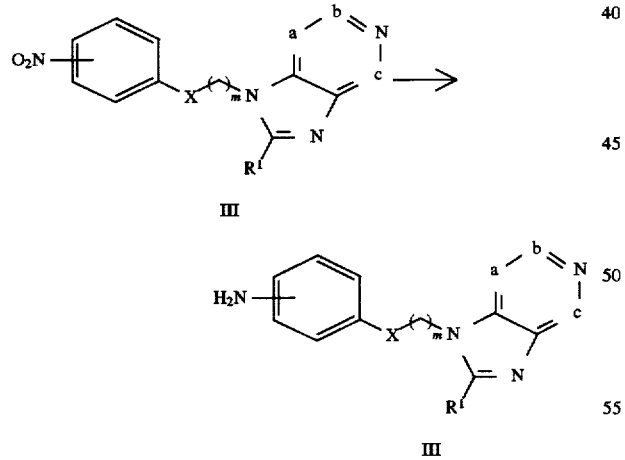

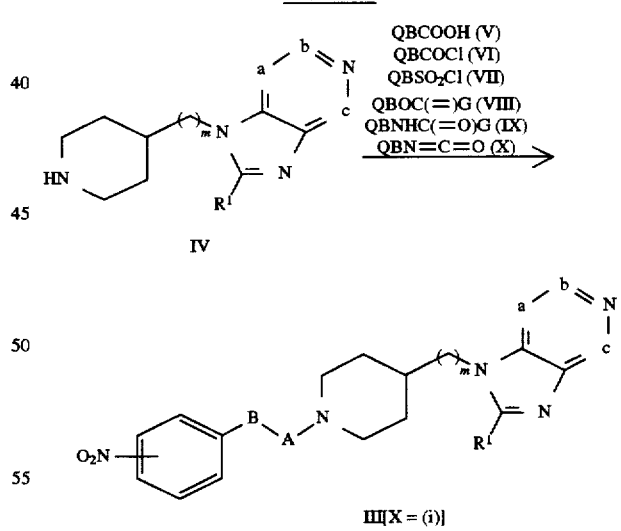

Scheme 1

QBCOOH (V)
QBCOCl (VI)
QBSO₂Cl (VII)
QBOC(=)G (VIII)
QBNHC(=O)G (IX)
QBN=C=O (X)

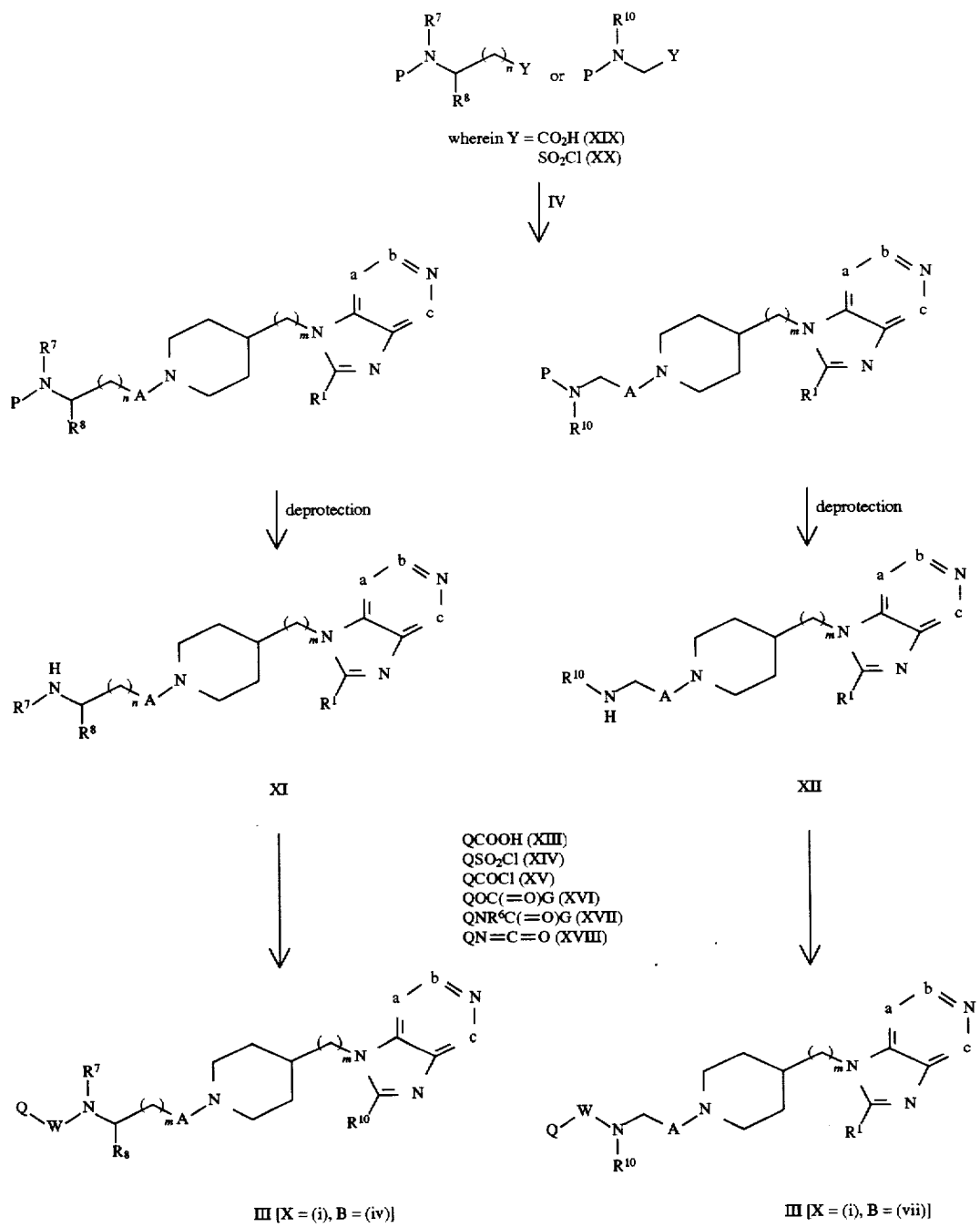

Scheme 3

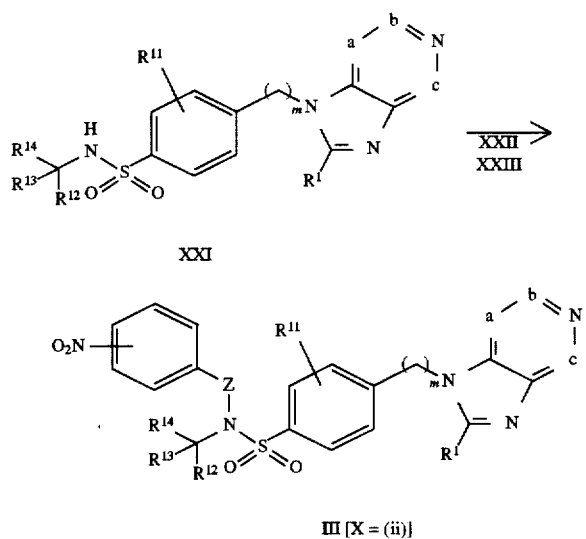

III [X = (ii)]

wherein:

the nitro group can be at the 3- or 4-position of the benzene ring;

Q represents a 3- or 4-nitrophenyl group;

G represents a good leaving group such as chloro or —OPh;

P represents an amino protecting group, such as a tert-butoxycarbonyl group;

Y represents a group $CO_2H$ (thus giving rise to acids of formula XIX) or a group $SO_2Cl$ (thus giving rise to sulfonyl chlorides of formula XX); and a, b, c, m, n, $R^1$, $R^7$, $R^8$, $R^{10}$, $R^{11}$, $R^{12}$, $R^{13}$, $R^{14}$, W and Z are as defined above.

Nitro compounds of formula III wherein X represents a group of formula (i) can be prepared in general from compounds of formula IV by reaction with an acid chloride of formula QBCOCl (VI), a sulfonyl chloride of formula QBSO₂Cl (VII), a compound of formula QBOC(=O)G (VIII), a compound of formula QBNHC(=O)G (IX) or a compound of formula QBN=C=O (X), as shown in Scheme 1. This reaction is carried out in the presence of a proton scavenger amine such as triethylamine or pyridine in a suitable solvent, or, alternatively, the base itself can also be used as solvent.

Examples of suitable solvents include halogenated hydrocarbons, such as dichloromethane and chloroform; ethers, such as diethyl ether, tetrahydrofuran and dioxane; and aromatic hydrocarbons, such as benzene and toluene. The reaction is carried out at a temperature preferably between 0° C. and that of the boiling point of the solvent. As an alternative to the acid chloride, the corresponding anhydride can be employed. Isocyanate derivatives of formula X may have been previously prepared or may be generated in situ from the corresponding acid derivative of formula QBCO₂H (V) by known procedures such as for example by treatment with diphenylphosphorylazide in the presence of triethylamine.

Alternatively, compounds of formula III wherein X represents a group of formula (i) and A represents —CO— can also be prepared by a dehydration procedure between an amine of formula IV and a carboxylic acid of formula QBCOOH (V). This process can be carried out using any conventional reaction of amide bond formation, such as for example by reacting an amine with an acid in the presence of an appropriate condensing agent such as a diimide, e.g. dicyclohexylcarbodiimide, alone or in combination with 1-hydroxybenzotriazole. This reaction is carried out in an inert solvent such as a halogenated hydrocarbon, for example dichloromethane or chloroform; an ether, for example tetrahydrofuran or dioxane; acetonitrile; or a substituted amide, for example dimethylformamide. The reaction is carried out at a temperature preferably comprised between 0° and 60° C. during a reaction time ranging preferably from 6 to 24 h.

Alternatively, compounds of formula III wherein X represents a group of formula (i) and B represents a group of formula (iv) or (vii) can be prepared from compounds of formula XI or XII by treatment with a compound of formula XIII–XVIII, as shown in Scheme 2. This reaction is carried out under the same experimental conditions mentioned above in connection with the conversion of IV into III.

Compounds of formula XI and XII can be prepared using the general procedure described in Scheme 1 for the synthesis of III but starting from an acid of formula XIX (or from its corresponding acid chloride or anhydride) or from a sulfonyl chloride of formula XX wherein the amino function is blocked with an amino protecting group (P), as shown in Scheme 2. As amino protecting groups it is possible to use any amino protecting group known in the art, such as those described in Greene T.W., "Protective Groups in Organic Synthesis", John Wiley & Sons, New York, 1981, for example a tert-butoxycarbony group. In this case, it will be necessary a subsequent step for removing the protecting group in order to obtain the compounds of formula XI and XII. Deprotection is carried out using known procedures, for example those described in the above general reference.

Nitro derivatives of formula III wherein X represents a group of formula (ii) can be prepared from a compound of formula XXI by reaction with an acid chloride of formula Q(CH₂)_qCOCl (XXII) or a compound of formula Q(CH₂)_rL (XXIII), wherein q and r are as defined above, Q represents a 4- or 3-nitrophenyl group and L represents a good leaving group such as chloro, bromo, iodo, methanesulfonyloxy, p-toluenesulfonyloxy or trifluoromethanesulfonyloxy, as shown in Scheme 3. This reaction is carried out by treatment with a base such as sodium hydride in a suitable aprotic sovlvent such as tetrahydrofuran, followed by treatment with a compound of formula XXII or XXIII, at a temperature preferably between 0° C. and that of the boiling point of the solvent.

Alternatively, amino compounds of formula II can also be obtained directly by using sequences analogous to those described in Schemes 1, 2 and 3 for the preparation of nitro compounds of formula III, as summarized in the following scheme:

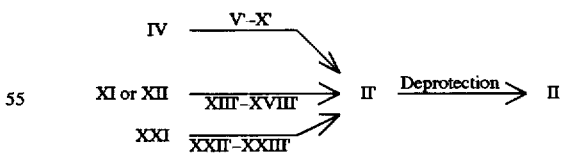

Thus, compounds of formula II may be prepared by treatment of an amine IV with a compound of formula V'–X' analogous to a compound V–X but having an amino substituent instead of a nitro group, under the same experimental conditions. Furthermore, compounds of formula II may also be obtained by reacting XI or XII with a compound XIII'–XVIII', that is, a compound analogous to XIII–XVIII but having an amino substituent instead of a nitro group, under the same experimental conditions. Likewise, a compound II may also be prepared by treatment of a compound XXI with a compound XXII' or XXIII', analogous to XXII and XXIII but with an amino group in place of the nitro group.

Although in some instances it will be possible to perform the above reactions directly using the amino group in unprotected form, in general it will be necessary or convenient to protect this amino group in order to avoid polymerization of the compounds V'-X', XIII-XVIII' and XXII'-XXIII'. Any amino protecting group available in the art can be employed here, such as those described in T.W. Greene (see above). In this case, amines of formula II are then obtained by deprotection of the protected amine II' under the reported conditions.

Compounds of formula IV may be prepared following the procedure disclosed in Scheme 4, which is shown below:

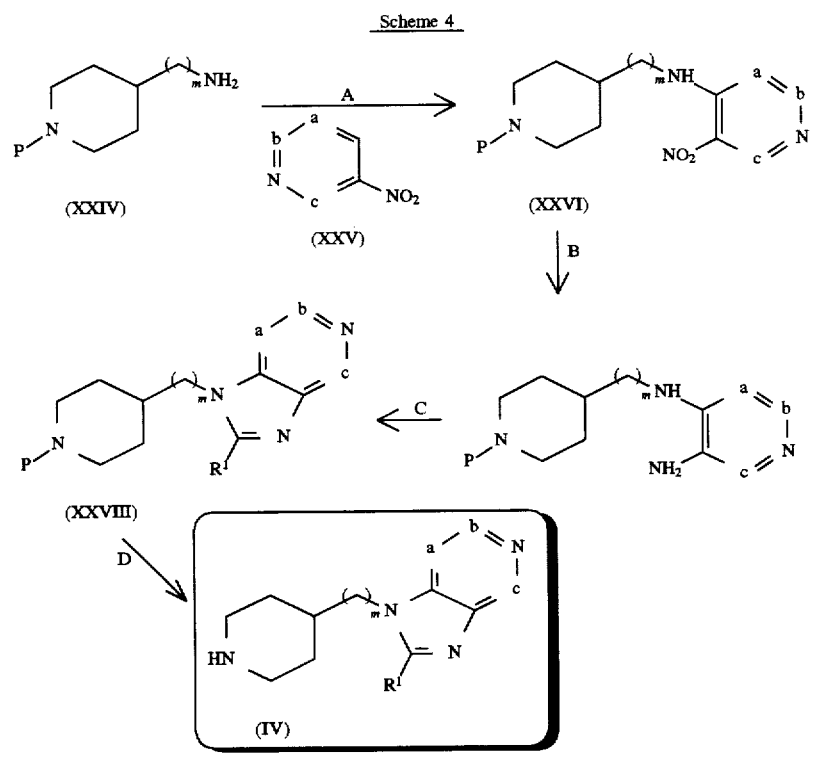

wherein a, b, c, m and $R^1$ are as defined above; P represents an amino protecting group such as for example a tert-butoxycarbonyl group and J represents halogen or $C_{1-6}$ alkoxy.

In a first step (step A), a compound of formula XXIV is allowed to react with a compound of formula XXV in the presence of a proton scavenger amine such as triethylamine in a suitable solvent such as a halogenated hydrocarbon, for example chloroform, at a suitable temperature, preferably between room temperature and that of the boiling point of the solvent, to give a compound of formula XXVI.

The reduction of a compound of formula XXVI (step B) leads to a compound of formula XXVII. This reduction can be carried out by hydrogenation in the presence of a catalyst such as palladium on carbon in a suitable solvent such as an alcohol at a temperature preferably between room temperature and that of the boiling point of the solvent, at a pressure preferably between atmospheric pressure and 10 atmospheres and during a reaction time preferably between 1 and 48 h. Alternatively, this reduction may be carried out using a suitable reducing agent such as $Na_2S_2O_4$ in a suitable solvent such as mixtures of water and an organic solvent, for example tetrahydrofuran, ethanol or pyridine.

In step C, a compound of formula XXVII is allowed to react with an imino ether salt of formula $R^1C(=NH)OR^{18}$.HT (XXIX, wherein $R^1$ has the previously described meaning, $R^{18}$ represents $C_{1-6}$ alkyl and T represents halogen) in a suitable solvent such as an alcohol, for example ethanol, to give a compound of formula XXVIII. This reaction is carried out at a temperature preferably between room temperature and that of the boiling point of the solvent, during a reaction time preferably between 6 and 48 h. Alternatively, instead of an imino ether it is possible to use a carboxylic acid of formula $R^1COOH$ (XXX), an acid halide of formula $R^1COT$ (XXXI), an anydride of formula $(R^1CO)_2O$ (XXXII) or a trialkylorthoester of formula $R^1C(OR^{18})_3$ (XXXIII), wherein $R^1$, T and $R^{18}$ have the previously described meaning.

Finally, deprotection of the piperidinic nitrogen atom of a compound of formula XXVIII (step D) leads to a compound of formula IV. The agent used for this deprotection and the reaction conditions employed will depend upon the nature of the protecting group present. Thus, if the protecting group is a tert-butoxycarbonyl group, deprotection can be carried out by treatment with an acid (for example an inorganic acid such as hydrochloric acid, phosphoric acid, sulfuric acid or the like or an organic acid such as toluenesulfonic acid, methanesulfonic acid, acetic acid, or trifluoroacetic acid) in a suitable solvent such as water, an alcohol (e.g. methanol), an ether (e.g. tetrahydrofuran or dioxane) or a halogenated hydrocarbon (e.g. dichloromethane), at a temperature preferably between 0° C. and room temperature.

Compounds of formula XXI can be prepared following the procedures disclosed in patent applications WO 92/03422 and WO 92/03423.

Acids of formula V, V', XIII, XIII' and XIX and sulfonyl chlorides of formula VII, VII', XIV, XIV' and XX are commercially available, widely described in the literature or can be prepared by widely used procedures, which are well known to those skilled in the art, starting from commercially available products or products which have already been reported in the literature. Examples of these procedures include alkylations, acylations, nitration of aromatic rings, conjugated additions to double bonds, Wittig reaction for the preparation of double bonds, preparation of sulfonamides, reductive aminations, and the like. All these reactions are known per se and are carried out in accordance with the reported conditions.

Compounds of formulae VIII, IX, XVI and XVII can be readily prepared from the corresponding alcohols and amines using conventional procedures, for example by treatment with phenyl chloroformate.

Isocyanates of formulae X and XVIII can be prepared from the corresponding acids of formula V and XIII, respectively, using a sequence which comprises the following steps: conversion of the acid to an acylazide by treatment for example with diphenylphosphorylazide; and subsequent Curtius rearrangement of said acylazide to give an isocyanate. This sequence for preparing isocyanates from carboxylic acids is widely described in the literature and can be carried out in accordance with the reported conditions.

Compounds of formulae XXII, XXIII, XXIV, XXV, and XXIX-XXXIII are commercially available, widely described in the literature or can be prepared by methods analogous to those disclosed in the art starting from commercially available products.

As mentioned above, certain compounds of the present invention may exhibit cis/trans isomerism, namely those compounds of formula I wherein X represents a group of formula (i) and B represents a group of formula (v). Frequently, these compounds are obtained as mixtures of the two isomers, which then need to be separated to afford the individual compounds in pure form. Although such a separation can be performed on the final products of formula I, it is preferable to carry it out at a previous stage in the synthesis, for example upon the corresponding compounds of formula II or V. Nevertheless, although it might be possible to obtain the individual isomers by separation from a mixture, it would be highly desirable to have available stereoselective methods for preparing these precursors.

A key intermediate in the preparation of one of the preferred compounds of this invention is cis 3-(4-nitrophenyl)-3-phenylpropenoic acid.

This type of compounds are prepared in general using the Wittig-Horner reaction under the standard conditions reported in the literature, which involves treating a benzophenone derivative, in this case 4- nitrobenzophenone, with triethylphosphonoacetate in the presence of a base such as sodium hydride at a temperature comprised between room temperature and that of the boiling point of the solvent. However, the resulting product from this reaction is always a mixture of the cis and trans isomers of 3-(4-nitrophenyl) -3-phenylpropenoic acid, which must then be separated to obtain the pure cis isomer. Recently, we have surprisingly found out that by modifying the experimental conditions of this reaction it is possible to obtain the cis isomer of this acid with a much higher stereoselectivity. This reaction also allows to obtain other cis-diphenylpropenoic acids having an electron-withdrawing group, such as a halogen, trifluoromethyl, ester or cyano group, at the 4-position of one of the two aromatic rings. To the best of our knowledge, this is the first report of a stereospecific Wittig reaction for benzophenone derivatives.

Therefore, it is a further object of the present invention to provide a new stereoselective process for preparing cis-3-(4-nitrophenyl)-3-phenylpropenoic acid, which comprises reacting 4-nitrobenzophenone with the anion of a $C_{1-6}$ alkyl trimethylsilylacetate, prepared by treatment of the $C_{1-6}$ alkyl trimethylsilylacetate with a bulky amidure, such as that generated by treatment of diisopropylamine, dicyclohexylamine or tetramethylpiperidine with butyllithium, at a temperature between $-78°$ C. and $-10°$ C. in a suitable solvent such as tetrahydrofuran, diethyl ether or dimethoxyethane, followed by hydrolysis of the resulting ester.

The compounds of the present invention are useful in the treatment or prevention of inflammatory bowel disease. As mentioned above, these compounds undergo bacterial cleavage in the colon, liberating 5-aminosalicylic acid and a PAF antagonist of formula II. The activity of the compounds of formula II as PAF antagonists can be tested using tests 1 and 2. The efficacy of the compounds of formula I in the treatment of inflammatory bowel disease can be determined using test 3.

Test 1-Inhibition of platelet aggregation induced by PAF.

Platelet aggregation studies were done by the method of Born (J. Physiol., 1962, 162 67). Blood was collected in 3.16% sodium citrate (1 volume per 9 volumes of blood) by cardiac puncture from male New Zealand rabbits (2–2.5 Kg body weight). Platelet rich plasma (PRP) was prepared by centrifuging the blood at 250xg for 10 min. at 4° C. PRP was diluted with platelet-poor plasma (PPP) obtained by further centrifuging at 3000xg for 10 min. The platelet count was adjusted to $3 \times 10^5$ cells/mm$^3$. Platelet aggregation was induced by $C_{18}$-PAF (15 nM) and was measured using an aggregometer Chronolog 560. Activity was expressed as the $IC_{50}$ value, that is to say the concentration of drug required to inhibit platelet aggregatory response by 50%. The results are shown in table I below, wherein the compounds tested are as follows:

compound A is the compound described in reference example 8;

compound B is the compound described in reference example 11a;

compound C is the compound described in reference example 11b;

compound D is the compound described in reference example 14;

compound E is the compound described in reference example 16;

compound F is the compound described in reference example 18;

compound G is the compound described in reference example 20.

TABLE I

| Compound No. | IC$_{50}$ (µM) |
|---|---|
| A | 0.019 |
| B | 0.018 |
| C | 0.005 |
| D | 0.075 |
| E | 0.030 |
| F | 0.012 |
| G | 0.016 |

Test 2- Inhibition of PAF-induced hypotension in normotensive rats.

Male Sprague-Dawley rats, weighing 180–220 g, were anesthetized with sodium pentobarbital (50 mg/Kg i.p.). Blood pressure was recorded from the left carotid artery using a Statham pressure transducer coupled to a Beckman R611 recorder. Right and left femoral veins were catheterized to inject test compounds and PAF (0.5 µg/Kg). Test compounds were administered by intravenous injection (1 mL/Kg, dissolved in saline) 3 min. before PAF.

Blood pressure was monitored and percent inhibition of PAF-induced hypotension with respect to controls was calculated. Results were expressed as $ID_{50}$ values, that is to say the dose of test compound required to inhibit hypotension by 50%. Results are shown in Table II, wherein the test compounds are identical to those described for test 1.

TABLE II

| Compound No | $ID_{50}$ (mg/Kg) |
|---|---|
| A | 0.099 |
| B | 0.029 |
| C | 0.01–0.025 |
| D | 0.088 |
| E | 0.15 |
| F | 0.033 |
| G | 0.14 |

Test 3- Trinitrobenzenesulfonic acid-induced inflammatory bowel disease in rats

Male Sprague-Dawley rats weighing 220–240 g were used. Animals were food fasted for 36 h before experimentation; during this time they were allowed to drink water containing per litre : 200 g of glucose; 0.30 g of NaCl; 74.6 mg of KCl and 15 mL of a preparation containing 2 mg/mL of sennosides A and B. Colitis was then induced by a single intracolonic instillation of trinitrobenzenesulfonic acid (TNBS, 60 mg in 1 mL of 20% ethanol). Treatment with test compounds was started two days before TNBS administration (day 0) and was continued throughout the experiment up to day 6. Test compounds were administered daily by gavage at a dose of 100 mg/Kg. At day 7 rats were subjected to an intracolonic dialysis in order to measure the intraluminal release of prostaglandin $E_2$ (PGE2), thromboxane $B_2$ ($TBX_2$) and leukotriene $B_4$ ($LTB_4$), which are used as inflammation markers. Eicosanoid concentration in the dialysates was determined by specific radioimmunoassay. Then, animals were killed and colonic damage was assessed both macroscopically and histologically according to pre-established criteria (Videla et al., Gut, 1994, 35: 1090–1097). The results obtained with the compound of example 3 are summarized in FIGS. 1–4.

Figure 1:
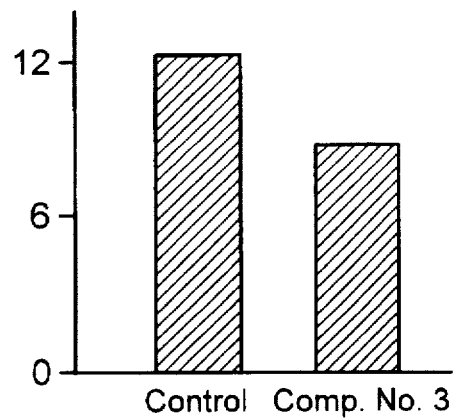
FIG. 1 shows the results of the total damage score (both macroscopic and histologic assessment) of colonic lesions at day 7.
Figure 2:
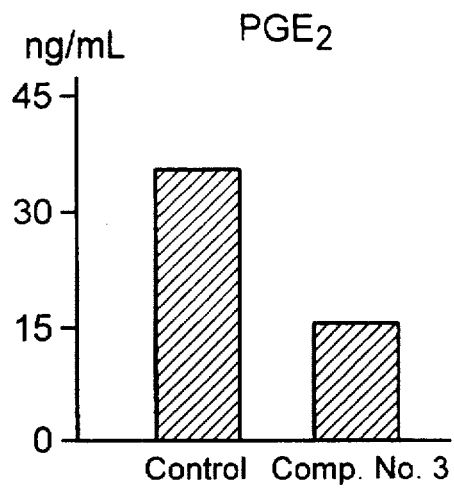
FIGS. 2, 3 and 4 show the intracolonic liberation of eicosanoids ($PGE_2$, $TXB_2$, and $LTB_4$) at day 7.
Figure 3:
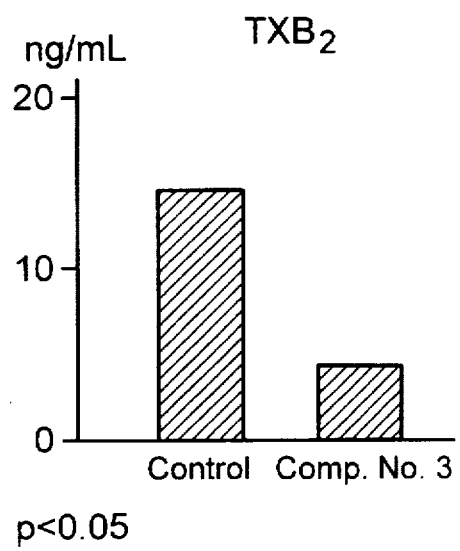
Figure 4:
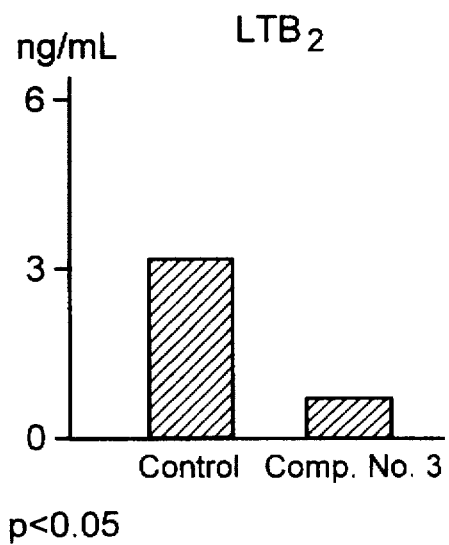

The results of these figures show that the administration of a compound of formula I significantly reduces the TNBS-induced colonic damage in comparison with the control group (p<0.05). Moreover, treatment with a compound of formula I also shows an effect on the release of the inflammation markers studied ($PGE_2$, $TXB_2$ and $LTB_4$) since it reduces significantly the intracolonic release of all of them (p<0.05 in the three cases). We have thus shown the effectiveness of the compounds of the present invention in the remission of the lesions caused by experimental induction of inflammatory bowel disease in the rat.

In accordance with the activity of the compounds herein disclosed, the present invention further provides compositions that comprise a compound of the invention together with an excipient and optionally other auxiliary agents, if necessary.

The products of the present invention will usually be administered by the oral route to mammals, including man.

However, they may be adapted for other modes of administration, for example parenteral or rectal administration, the latter being the route of choice for patients with inflammatory bowel disease localized in the rectum.

Solid compositions according to the present invention for oral administration include compressed tablets, dispersible powders, granules and capsules. In tablets, the active component is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a local action at the colon. Gastric film-coated or enteric film-coated tablets can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are also possible, wherein the active ingredient is mixed with water or an oily medium, for example coconut oil, liquid paraffin or olive oil.

Dispersible powders and granules suitable for the preparation of a suspension by the addition of water provide the active ingredient in admixture with dispersing or wetting agents, suspending agents, such as sodium carboxymethylcellulose, methylcellulose, hydroxypropylmethylcellulose, sodium alginate, polyvinylpyrrolidone, gum tragacanth, xantham gum, gum acacia, and one or more preservatives, such as methyl or propyl p-hydroxybenzoate. Additional excipients, for example sweetening, flavouring and colouring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavouring, preserving agents and buffers.

Preparations for injection, according to the present invention, for parenteral administration include sterile aqueous or non-aqueous solutions, suspensions or emulsions, in a non-toxic parentally-acceptable diluent or solvent. Examples of aqueous solvents or suspending media are distilled water for injection, Ringer's solution, and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by any known method or manufactured in the form of sterile solid compositions which can be dissolved in sterile water or some other sterile injectable medium immediately before use. When all of the components are sterile, the injectables will maintain sterility if they are manufactured under a sterile environment.

The products of the present invention may also be administered rectally in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides.

The dosage and frequency of dose may vary depending upon symptoms, age and body weight of the patient, as well as upon the route of administration. For example, the compounds of the invention may be administered orally or rectally to human patients at a daily dosage of from about 10 to about 10000 mg for an adult, preferably a dosage of 100–5000 mg, which may be administered either as a single dose or as divided doses. However, in special cases and at the discretion of the attending physician, doses outside the broader margins may be required.

Following are cited some examples of representative formulations for tablets, capsules, syrups, enemas and injectables. They can be prepared following standard procedures and are useful in the treatment of inflammatory bowel disease.

| Tablets | | |
|---|---|---|
| Compound of formula I | 500 | mg |
| Dibasic calcium phosphate | 125 | mg |
| Sodium starch glycolate | 10 | mg |
| Talc | 12.5 | mg |
| Magnesium stearate | 2.5 | mg |
| | 650.0 | mg |
| Hard gelatin capsules | | |
| Compound of formula I | 500 | mg |
| Lactose | 197 | mg |
| Magnesium stearate | 3 | mg |
| | 700 | mg |
| Syrup | | |
| Compound of formula I | 4 | g |
| Sucrose | 45 | g |
| Flavouring agent | 0.2 | g |
| Sweetening agent | 0.1 | g |
| Water to | 100 | mL |
| Enema | | |
| Compound of formula I | 2 | g |
| Monosodium phosphate | 18 | g |
| Disodium phosphate | 8 | g |
| Sorbic acid | 0.1 | g |
| Preservative agent | 0.1 | g |
| Water to | 100 | mL |
| Injectable | | |
| Compound of formula I | 200 | mg |
| Benzylic alcohol | 0.05 | ml |
| Propylene glycol | 1 | ml |
| Water to | 5 | ml |

The following examples illustrate, but do not limit, the scope of the present invention.

REFERENCE EXAMPLE 1

1-tert-Butoxycarbonyl-4-(aminomethyl)piperidine

To a cooled (0° C.) solution of 4-(aminomethyl)piperidine (40 g, 0.35 mol) in $CHCl_3$ (300 mL) was added a solution of di-tert-butyl dicarbonate (39.2 g, 0.17 mol) in $CHCl_3$ (300 mL) and the reaction mixture was stirred at room temperature for 48 h. The resulting solution was washed with $H_2O$ and the aqueous phase was reextracted with $CHCl_3$. The combined organic phases were dried over sodium sulphate and the solvent was removed to afford 54.1 of a crude product, which was directly used in the next step as obtained. $^1H$ NMR (80 MHz, $CDCl_3$) δ(TMS): 4.11 (broad d, J=13.4 Hz, 2H), 2.69 (m, 4H), 1.45 (s, 9H), 1.8–0.8 (complex signal, 7H).

REFERENCE EXAMPLE 2

4-[[1-(tert-Butoxycarbonyl)-4-piperidyl]methylamino]-3-nitropyridine

To a cooled (0° C.) solution of the product obtained in reference example 1 (34.66 g, 0.16 mol) and triethylamine (24.75 mL) in CHCl3 (300 mL) was added 4-chloro-3-nitropyridine (30.7 g, 0.19 mol) in $CHCl_3$ (250 mL) and the mixture stirred at room temperature for 48 h. The resulting solution was washed with 0.5N NaOH and the aqueous phase was reextracted with $CHCl_3$. The combined organic extracts were dried over sodium sulfate and concentrated to afford 63 g of a crude product. This was purified by chromatography on silica gel (EtOAc), to afford 26.3 g (48%) of a yellow solid. $^1H$ NMR (80 MHz, CDCl3) δ(TMS): 9.20 (s, 1H), 8.30 (d, J=5.5 Hz, 1H), 8.19 (m, 1H), 6.72 (d, J=5.5 Hz, 1H), 4.18 (broad d, J=13.4 Hz, 2H), 3.26 (t, J=5.9 Hz, 2H), 2.72 (broad t, J=12.7 Hz, 2H), 1.46 (s, 9H), 1.8–0.8 (complex signal, 5H).

REFERENCE EXAMPLE 3

3-Amino-4-[[1-(tert-butoxycarbonyl)-4-piperidyl]methylamino]pyridine

A solution of the product obtained in reference example 2 (26.2 g, 0.077 mol) in MeOH (500 mL) was hydrogenated at atmospheric pressure in the presence of 10% Pd/C (3.83 g) for 18 h. The catalyst was filtered off and the filtrate concentrated to a crude product (22.9 g, 96%), which was directly used in the next step as obtained.

$^1H$ NMR (80 MHz, $CDCl_3$) δ(TMS): 7.65 (d, J=5.5 Hz, 1H), 7.64 (s, 1H), 6.59 (d, J=5.5 Hz, 1H), 4.10 (broad d, J=13.4 Hz, 2H), 3.9 (s, 3H), 3.25 (d, J=6.5 Hz, 2H), 2.74 (broad t, J=12.0 Hz, 2H), 1.46 (s, 9H), 1.8–0.8 (complex signal, 5H).

REFERENCE EXAMPLE 4

1-[[1-(tert-Butoxycarbonyl)-4-piperidyl]methyl]-1H-2-methylimidazo[4,5-c]pyridine To a solution of the product obtained in reference example 3 (22.9 g, 0.07 mol) in EtOH (350 mL) was added ethyl acetimidate hydrochloride (9.2 g, 0.074 mol) and the mixture was refluxed for 4 h. A second equivalent of ethyl acetimidate hydrochloride was added (9.2 g, 0.074 mol) and the mixture was further refluxed for 18 h. Finally, a third equivalent of ethyl acetimidate hydrochloride was added (9.2 g, 0.074 mol) and the mixture was heated for 4 h more. The resulting solution was concentrated in vacuo and the residue partitioned between $CHCl_3$ and 0.5N NaOH. The organic phase was dried over sodium sulfate and concentrated to a residue (30 g), which was purified by chromatography on silica gel ($CHCl_3$:MeOH, 10%) to afford the title compound as a yellow solid (23.4 g, 95%). $^1H$ NMR (80MHz, $CDCl_3$) δ (TMS): 8.98 (s, 1H), 8.38 (d, J=5.5 Hz, 1H), 8.22 (d, J=5.5 Hz, 1H), 4.10 (broad d, J=13.4 Hz, 2H), 3.96 (d, 1=7.3 Hz, 2H), 2.64 (broad t, J=12.7 Hz, 2H), 2.63 (s, 3H), 1.46 (s, 9H), 2.2–1.0 (complex signal, 5H).

REFERENCE EXAMPLE 5

1-[(4-Piperidyl)methyl]-1H-2-methylimidazo[4,5-c]pyridine

To a cooled (0° C.) solution of the product obtained in reference example 4 (23.1 g, 0.07 mol) in MeOH (200 mL)

was added dropwise 6.5N HCl(g)/dioxane solution (44 mL). After the addition was finished, the mixture was stirred at room temperature for 2 h and evaporated to dryness.

The residue was cooled in an ice bath. 1N NaOH was added and the resulting solution was extracted with CHCl$_3$ (3x). The combined organic extracts were dried over sodium sulfate and concentrated to a yellow solid (15.8 g, 98%). $^1$H NMR (80MHz, CDCl$_3$) δ (TMS): 8.96 (s, 1H), 8.35 (d, 1=5.5 Hz, 1H), 7.20 (d, J=5.5 Hz, 1H), 3.95 (d, J=7.3 Hz, 2H), 3.06 (broad d, 1=12.0 Hz, 2H), 2.61 (s, 3H), 2.51 (broad t, J=12.7 Hz, 2H), 2.2-1.0 (complex signal, 6H).

REFERENCE EXAMPLE 6

3-Methyl-3-(4-nitrophenyl)butanoic acid a) 3-Methyl-3-phenylbutyronitrile

A mixture of 1-chloro-2-methyl-2-phenylpropane (150 g, 0.889 mol) and NaCN (54.46 g) in DMSO (250 mL) was heated at 100 ° C for 3 weeks. The resulting solution was concentrated to half the initial volume. H$_2$O (400 mL) was added and it was extracted with Et$_2$O (3x). The combined organic extractes were dried and concentrated to a crude product (115.1 g), which was directly used in the next step as obtained.

b) 3-Methyl-3-phenylbutanoic acid

To the product obtained in a) above was added slowly H$_2$O (375 mL) and H$_2$SO$_4$ (300 mL), and the mixture was refluxed for 48 h. Next, H$_2$O was added and the resulting solution was extracted with CHCl$_3$. The organic phase was washed with 2N NaOH (3x), and the aqueous phase was acidified with 5N HCl and extracted with CHCl$_3$. The combined organic extracts were dried and concentrated to afford the title product. $^1$H NMR (80MHz, CDCl$_3$) δ (TMS): 10.8 (m, 1H), 7.29 (s, 5H), 2.61 (s, 2H), 1.43 (s,6H).

c) Title compound

To cooled (0° C) concentrated H$_2$SO$_4$ (18.5 mL), was added 3-methyl-3- phenylbutanoic acid (10 g, 56 mmol). Next, a cooled solution of HNO$_3$ (3 mL) in H$_2$SO$_4$ (6.2 mL) was added dropwise and the reaction mixture was stirred at 0° C. for 30 min and then at room temperature for 30 min more. The mixture was poured into ice and the resulting solution was allowed to stand in the refrigerator overnight. The precipitate was filtered, washed with H$_2$0 and dried, to afford a crude product (14.5 g). This was purified by chromatography on silica gel (CHCl$_3$:MeOH, 3%) to give the title compound (5.9 g, 47%). $^1$H NMR (80MHz, CDCl$_3$) δ (TMS): 8.16 (d, J=6.5 Hz, 2H), 7.55 (d, J=6.5 Hz, 2H), 3.5 (m, 1H), 2.70 (s, 2H), 1.50 (s, 6H).

REFERENCE EXAMPLE 7

1-[[1-[3-Methyl-3-(4-nitrophenyl)butanoyl]-4-piperidyl]methyl]-1H-2- methylimidazo[4,5-c] pyridine To a mixture of the product obtained in reference example 5 (6 g, 26 mmol), 3-methyl-3-(4-nitrophenyl)butanoic acid (5.8 g, 26 mmol, obtained in reference example 6) and 1-hydroxybenzotriazole (3.64 g) in DMF (180 mL), was added at 0° C. and under a nitrogen atmosphere dicyclohexylcarbodiimide (5.28 g) and the reaction mixture was stirred at room temperature for 18 h.

The white insoluble material was filtered off and the solvents were removed in vacuo. The residue was taken up in chloroform and washed with saturated NaHCO$_3$ solution, water and brine, dried and concentrated. The residue (8.3 g) was purified by chromatography on silica gel (CHCl$_3$:MeOH, 10%), to afford 3.21 g of the title compound as an oil (28%). $^1$H NMR (80MHz, CDCl$_3$) δ (TMS): 8.96 (s, 1H), 8.37 (d, J=5.5 Hz, 1H), 8.11 (d, J=8.4 Hz, 2H), 7.51 (d, J=8.4 Hz, 2H), 7.18 (d, J=5.5 Hz, 1H), 4.55 (m, 1H), 3.95 (d, J=7.1 Hz, 2H), 3.83 (m, 1H), 2.59 (s, 3H), 3-0.5 (complex signal, 9H), 1.50 (s, 6H).

REFERENCE EXAMPLE 8

1-[[1-[3-(4-Aminophenyl)-3-methylbutanoyl]-4-piperidyl]methyl]-1H-2- methylimidazo[4,5-c] pyridine A solution of the product obtained in reference example 7 (2.27 g, 5.2 mmol) in MeOH (100 mL) was hydrogenated at atmospheric pressure in the presence of 10% Pd/C (0.25 g) for 18 h. The catalyst was filtered off and the solvent was removed to afford 1.26 g of a crude product. This was purified by chromatography on silica gel (CHCl$_3$:MeOH, 10%) to yield 1.1 g of the title compound as a white solid (52%). mp: 172°–173° C. (C$_{24}$H$_{31}$N$_5$0.0.75H$_2$O);

$^1$H NMR (80MHz, CDCl$_3$) δ (TMS): 8.96 (s, 1H), 8.38 (d, J=5.5 Hz, 1H), 7.18 (m, 3H), 6.62 (d, J=5.5 Hz, 2H), 4.65 (m, 1H), 3.86 (d, J=7.1 Hz, 2H), 3.63 (m, 2H), 3.50 (m, 1H), 2.59 (s, 3H), 3-0.5 (complex signal, 9H), 1.25 (s, 6H).

REFERENCE EXAMPLE 9 cis and trans 3-(4-Nitrophenyl)-3-phenylpropenoic acid

To a cooled (0° C) suspension of 50% NaH (24.66 g, 0.51 mol) in THF (375 mL) was added dropwise triethyl phosphonoacetate (88.2 mL, 44 mmol).

The mixture was stirred for 45 min and 4-nitrobenzophenone (102 g, 0.45 mmol) in THF (525 mL) was added. The resulting mixture was refluxed for 18 h under an argon atmosphere, and then allowed to cool and partitioned between H$_2$O and EtOAc. The organic phase was dried and concentrated to a residue (115 g). This crude material was dissolved in MeOH (600 mL), a solution of K$_2$CO$_3$ (87.2 g) in H$_2$O (288 mL) was added and the resulting mixture was refluxed for 4 h. MeOH was removed, water was added and the solution extracted with hexane. The aqueous solution was then brought up to acid pH with 5N HCl and extracted with CHCl$_3$. Evaporation of the solvent afforded a brown solid as a mixture of the cis and trans isomers in a 6:4 ratio.

$^1$H NMR (80MHz, CDCl$_3$) δ (TMS): 8.20 (m, 2H), 7.33 (m, 7H), 6.70 (m), 6.44 (s, 0.6 H), 6.38 (s, 0.4 H).

Pure cis isomer can be obtained by recrystallization from EtOAc (34 g, 30%). $^1$H NMR (80MHz, CDCl$_3$) δ (TMS): 8.23 (d, J=8.0 Hz, 2H), 7.33 (m, 7H), 6.70 (m), 6.44 (s, 1H).

Alternatively, pure cis isomer can be stereoselectively prepared as follows: To a cooled (−78° C.) solution of BuLi 1.6 M in hexane (60 mL, 0.096 mol) in 200 mL of dry THF, was added dropwsise dicyclohexylamine (19.2 mL) and the resulting solution was stirred at −78° C. for 30 min. Next, ethyl trimethylsilylacetate (17.46 mL, 0.095 mol) was added dropwise and after 30 min stirring 4-nitrobenzophenone (20.7 g, 0.091 mol) in THF (250 mL) was added. The resulting mixture was stirred for 30 min at −78° C. and then allowed to warm up to room temperature. The solvent was removed and the residue was partitioned between 0.5N HCl and EtOAc. The insoluble material was filtered off and discarded, and the organic phase was separated, dried and evaporated to give 35 g of a crude product. HPLC analysis (Licrospher 100CN column, eluent: MeOH-phosphate buffer pH=6.8, 40:60, UV detection at λ=220, flux of 1 mL/min) showed a 8:1 cis/trans isomer ratio together with 10% of starting ketone. This crude product was dissolved in 153 mL of MeOH, a solution of $K_2CO_3$ (26.5 g) in water (74 mL) was added and the resulting mixture was refluxed for 18 h. MeOH was removed, and the residue was acidified with 5N HCl and extracted with $CHCl_3$. The organic solution was dried and concentrated to afford 30 g of a crude product. This was recrystallized from EtOH (100 mL) to give 16 g (66% for the two steps) of the cis isomer (containing only 1% of trans isomer, as shown by HPLC analysis using a Licrospher RP-18 column, MeOH-phosphate buffer pH=3 60:40, UV detection at λ- 220, flux 1 mL/min).

Pure trans isomer can be obtained as follows: A mixture of ethyl trans- cinnamate (4.4g, 27 mmol), 4-bromonitrobenzene (6 g, 29.7 mol), triphenylphosphine (0.26 g), tributylamine (8 mL), and palladium acetate (57 mg) in acetonitrile (20 mL) was heated under argon at reflux for two days.

The cooled mixture was partitioned between 0.5 N NaOH and $CHCl_3$, the organic phase separated, dried and concentrated. The residue was purified by chromatography on silica gel (Hexane:EtOAc, 20%) to afford a white solid (2.4 g, 31 %). $^1$H NMR (80MHz, $CDCl_3$) δ (TMS): 8.18 (d, J=8.0 Hz, 2H), 7.33 (m, 8H), 6.39 (s, 1H).

REFERENCE EXAMPLE 10 cis and trans 1-[[1-[3-(4-Nitrophenyl)-3-phenylpropenoyl]-4-piperidyl]methyl]- 1H-2-methylimidazo[4,5-c]pyridine Following the procedure descrbed in reference example 7, but using a cis/trans mixture of 3-(4-nitrophenyl)-3-phenylpropenoic acid (obtained in reference example 9), the title compound was obtained as a white solid (85%). mp: 106-112° C ($C_{28}H_{27}N_5O_3$.0.5$H_2O$);

$^1$H NMR (80MHz, $CDCl_3$) δ (TMS): 8.95 (s, 1H), 8.37 (d, J=5.5 Hz, 1H), 8.18 (dd, J=8.6 Hz, J=3.2 Hz, 2H), 7.37 (m, 8H), 6.49 (s, 0.5H), 6.40 (s, 0.5H), 4.66 (m, 1H), 3.84 (m, 3H), 2.57 (s, 3H), 2.8-0.5 (complex signal, 7H).

REFERENCE EXAMPLE 11a and 11b a) cis -1-[[1-[3-(4-Aminophenyl)-3-phenylpropenoyl]-4-piperidyl]methyl]-1H-2-methylimidazo[4,5-c]pyridine b) trans -1-[[1-[3-(4-Aminophenyl)-3-phenylpropenoyl]-4-piperidyl]methyl]-1H-2-methylimidazo[4,5-c]pyridine Following the procedure described in reference example 8, but starting from the compound obtained in reference example 10, the title compound was obtained as a cis/trans mixture of isomers, which were separated by chromatography on silica gel ($CHCl_3$:MeOH, 10%) to afford:

A slower eluting isomer, isomer cis (reference example 11a)(54%):

mp: 121°-135° C.($C_{28}H_{29}N_5O$.3/2$H_2O$);

$^1$H NMR (80 MHz, $CDCl_3$) δ (TMS): 8.95 (s, 1H), 8.36 (d, J=5.5 Hz, 1H), 7.29 (s, 5H), 7.07 (m, 3H), 6.65 (d, J=6.5 Hz, 2H), 6.07 (s, 1H), 4.70 (m, 1H), 3.82 (m, 3H), 2.57 (s, 3H), 2.8-0.5 (complex signal, 9H).

A faster eluting isomer, isomer trans (reference example 11b) (22%):

mp: 223°-224° C.($C_{28}H_{29}N_5O$.1/2$H_2O$); $^1$H NMR (80 MHz, $CDCl_3$) δ (TMS): 8.96 (s, 1H), 8.38 (d, J=5.5 Hz, 1H), 7.30 (s, 5H), 7.05 (m, 3H), 6.60 (d, J=6.5 Hz, 2H), 6.17 (s, 1H), 4.60 (m, 1H), 3.81 (m, 3H), 2.55 (s, 3H), 2.8-0.5 (complex signal, 9H).

Following the same procedure described in reference example 10 but using pure cis or trans-3-(4-nitrophenyl)-3-phenylpropenoic acid (described in reference example 9) instead of a cis/trans mixture and then reducing the resulting compounds as described above, the title compound was obtained in pure cis or trans form.

REFERENCE EXAMPLE 12

1-[[1-(N-Phenylamino)acetyl-4-piperidyl]methyl]-1H-2-methylimidazo[4,5-c]pyridine A solution of 1-[[1-[(N-tert-butoxycarbonyl)-N-phenylamino]acetyl-4-piperidyl]methyl]-1H-2-methylimidazo[4,5-c]pyridine (3.9 g, 8.4 mmol) (obtained from the product of reference example 5 and [N-(tert-butoxycarbonyl)-N-phenylamino]acetic acid following the procedure described in reference example 7) in MeOH (60 mL) was treated with 6.2N HCl(g)/dioxan solution (7.5 mL) for 2.5 h at room temperature. The solvent was removed, the residue was made basic with 1N NaOH and extracted with chloroform. The organic solution was dried and concentrated to afford 2.5 g (86%) of the title product, which was directly used in the next step as obtained.

$^1$H NMR (80 MHz, $CDCl_3$+$CD_3OD$) δ (TMS): 8.88 (s, 1H), 8.33 (d, J=5.5 Hz, 1H), 7.35 (m, 4H), 6.70 (m, 2H), 4.64 (m, 1H), 3.98 (m, 5H), 2.63 (s, 3H), 3.1-1.0 (complex signal, 8H).

REFERENCE EXAMPLE 13

1-[[1-[[N-(4-Nitrophenylsulfonyl)-N-phenylamino]acetyl-4-piperidyl]methyl]-1H-2-methylimidazo[4,5c]pyridine To a solution of the product obtained in reference example 12 (2.5 g, 6.9 mmol) in pyridine (40 mL) was added 4-nitrobenzenesulfonyl chloride (1.54 g) and the resulting mixture was heated at 60° C. for 18 h. Solvents were removed and the resulting residue was partitioned between 0.5N NaOH and chloroform. The organic phase was separated, dried and concentrated to a crude product. This was purified by chromatography on silica gel ($CHCl_3$:MeOH 10%) to yield 2.93 g of a yellow solid (78%).

mp: 110°-115° C. ($C_{27}H_{28}N_6O_5S$.1/2$H_2O$)

$^1$H NMR (80 MHz, $CDCl_3$+$CD_3OD$) δ (TMS): 8.99 (s, 1H), 8.39 (d, J=5.5 Hz, 1H), 8.25 (d, J=8.8 Hz, 2H), 7.82 (d, J=8.8 Hz, 2H), 7.25 (m, 6H), 4.54 (m, 1H), 4.52 (s, 2H), 3.98 (d, J=7.2 Hz, 2H), 3.90 (m, 1H), 2.62 (s, 3H), 3.3-1.0 (complex signal, 7H).

REFERENCE EXAMPLE 14

11 [[1-[[N-(4-Aminophenylsulfonyl)-N-phenylamino]acetyl-4-piperidyl]methyl]-1H-2-methylimidazo[4,5-c]pyridine Following the procedure described in reference example 8, but starting from the compound obtained in reference example 13, the title compound was obtained as a white solid (78%).

mp: 147°-157° C. ($C_{27}H_{30}N_6O_3S$.$H_2O$)

$^1$H NMR (80 MHz, $CDCl_3$) δ (TMS): 8.79 (s, 1H), 8.38 (d, J=5.5 Hz, 1H), 7.45 (d, J=8.8 Hz, 2H), 7.26 (m, 6H), 6.94

(d, J=8.8 Hz, 2H), 4.36 (m, 1H), 4.35 (s, 2H), 4.00 (d, J=7.2 Hz, 2H), 3.98 (m, 1H), 2.63 (s, 3H), 3.3–1.0 (complex signal, 9H).

REFERENCE EXAMPLE 15

N-(4-Nitrobenzoyl)-N-[4-(1H-2-methylimidazo[4,5-c]pyridylmethyl)-phenylsulfonyl]-L-leucine ethyl ester To a solution of N-[4-(1H-2-methylimidazo[4,5-c]pyridylmethyl)phenylsulfonyl]-L-leucine ethyl ester (2.4 g, 5.4 mmol, obtained as described in WO 92/03423) in dry THF (80 mL), was added 50% NaH (0.23 g) and the resulting mixture was heated at 50° C. for 1.5 h. Then it was allowed to cool to room temperature, 4-nitrobenzoyl chloride (1.2 g, 6.4 mmol) in THF (20 mL) was added and the mixture was stirred for 52 h. The solvent was removed, and the residue was partitioned between 0.5N NaOH and chloroform. The organic phase was separated, dried and concentrated to afford 2.8 g of a crude product. This was purified by column chormatography ($CHCl_3$:MeOH, 10%) to afford 1.9 g of the title compound (65%).

mp: 68°–71° C.($C_{29}H_{31}N_5O_7S$);

$^1$H NMR (80 MHz, $CDCl_3$) δ (TMS): 9.02 (s, 1H), 8.40 (d, J=5.5 Hz, 1H), 8.11 (d, J=8.8 Hz, 2H), 7.87 (d, J=8.8 Hz, 2H), 7.53 (d, 1=8.8 Hz, 2H), 7.11 (d, J=8.8 Hz, 2H), 7.10 (d, J=5.5 Hz, 1H), 5.38 (s, 2H), 4.85 (t, J=6.7 Hz, 1H), 4.28 (q, J=7.1 Hz, 2H), 2.58 (s, 3H), 2.11 (t, J=6.7 Hz, 2H), 1.78 (quint, J=6.7 Hz, 1H), 1.30 (t, J=7.1 Hz, 3H), 0.94 (d, J=7.3 Hz, 3H), 0.86 (d, J=7.3 Hz, 3H).

REFERENCE EXAMPLE 16

N-(4-Aminobenzoyl)-N-[4-(1H-2-methylimidazo[4,5-c]pyridylmethyl)phenylsulfonyl]-L-leucine ethyl ester A solution of the product obtained in reference example 15 (1.91 g, 0.0032 mol) in MeOH (100 mL) was hydrogenated at atmospheric pressure in the presence of 10% Pd/C (0.3 g) for 18 h. The catalyst was filtered off and the solvent was removed, to afford 1.62 g of a crude product. This was purified by column chormatography ($CHCl_3$:MeOH:$NH_3$, 60:4:0.2) to yield 0.6 g (33%) of a white solid.

mp: 91°–94° C.($C_{29}H_{33}N_5O_5S$);

$^1$H NMR (80 MHz, $CDCl_3$) δ (TMS): 9.00 (s, 1H), 8.35 (d, J=5.5 Hz, 1H), 7.98 (d, J=8.8 Hz, 2H), 7.32 (d, J=8.8 Hz, 2H), 7.10 (m, 3H), 6.40 (d, J=8.8 Hz, 2H), 5.33 (s, 2H), 4.95 (dd, J=8.0 Hz, J=4.5 Hz, 1H), 4.20 (q, J=7.1 Hz, 2H), 2.54 (s, 3H), 2.0 (m, 5H), 1.32 (t, J=7.1 Hz, 3H), 0.86 (d, 1=7.3 Hz, 3H), 0.74 (d, J=7.3 Hz, 3H).

REFERENCE EXAMPLE 17

N-(4-Nitrobenzyl)-N-[4-(1H-2-methylimidazo[4,5-c]pyridylmethyl)-phenylsulfonyl]-L-leucine ethyl ester To a solution of N-[4-(1H-2-methylimidazo[4,5-c]pyridylmethyl)-phenylsulfonyl]-L-leucine ethyl ester (3 g, 6.7 mmol, obtained as described in WO 92/03423) in dry THF (30 mL), cooled in an ice bath, was added 50% NaH (0.28 g) and the resulting mixture was stirred at 0° C. for 0.5 h. Next, a solution of 4-nitrobenzyl mesylate (2.3 g, 9.9 mmol) in THF (20 mL) was added and the reaction mixture was stirred at room temperature for 18 h. The solvent was removed, and the residue was partitioned between 0.5N NaOH and chloroform. The organic phase was separated, dried and concentrated to afford 6 g of a crude product. This was purified by column chromatography ($CHCl_3$:MeOHN$H_3$, 60:2:0.2) to give 2.12 g (55%) of a yellow solid.

mp: 60°–65° C.($C_{29}H_{33}N_5O_6S.0.5H_2O$);

$^1$H NMR (80 MHz, $CDCl_3$) δ (TMS): 9.03 (s, 1H), 8.48 (d, J=5.5 Hz, 1H), 8.15 (d, J=8.7 Hz, 2H), 7.75 (d, J=8.7 Hz, 2H), 7.57 (d, J=8.7 Hz, 2H), 7.17 (m, 3H), 5.40 (s, 2H), 4.65 (AB system, J=17 Hz, J=25 Hz, 2H), 4.50 (m, 1H), 3.79 (m, 2H), 2.60 (s, 3H), 1.43 (m, 3H), 1.00 (t, J=7.1 Hz, 3H), 0.87 (d, J=5.6 Hz, 3H), 0.58 (d, J=5.6 Hz, 3H).

REFERENCE EXAMPLE 18

N-(4-Aminobenzyl)-N-[4-(1H-2-methylimidazo[4,5-c]pyridylmethyl)-phenylsulfonyl]-L-leucine ethyl ester Following the procedure described in reference example 16, but starting from the compound obtained in reference example 17, the title compound was obtained as a white solid (43%).

mp: 69°–73° C.($C_{29}H_{35}N_5O_4S$);

$^1$H NMR (80 MHz, $CDCl_3$) δ (TMS): 9.01 (s, 1H), 8.36 (d, J=5.5 Hz, 1H), 7.69 (d, J=8.7 Hz, 2H), 7.12 (m, 5H), 6.49 (d, J=8.7 Hz, 2H), 5.36 (s, 2H), 4.58 (m, 1H), 4.35 (AB system, J=15.7 Hz, J=28 Hz, 2H), 3.80 (m, 2H), 3.60 (m, 2H), 2.58 (s, 3H), 1.47 (m, 3H), 1.00 (t, J=7.1 Hz, 3H), 0.81 (d, J=5.6 Hz, 3H), 0.60 (d, J=5.6 Hz, 3H).

REFERENCE EXAMPLE 19

N-(4-Nitrobenzyl)-N-[(S)-1-isobutyl-2-ethoxyethyl]-4-1H-2-methylimidazo[4,5-c]pyridylmethyl)phenylsulfonamide Following the procedure described in reference example 17, but using N-[(S)-1-isobutyl-2-ethoxyethyl]-4-(1H-2-methylimidazo[4,5-c]pyridylmethyl)phenylsulfonamide (obtained as described in WO 92/03422), the title compound was obtained as a yellow oil (48%).

$^1$H NMR (80 MHz, $CDCl_3$) δ (TMS): 9.03 (s, 1H), 8.38 (d, J=5.5 Hz, 1H), 8.10 (d, J=8.7 Hz, 2H), 7.75 (d, J=8.7 Hz, 2H), 7.52 (d, J=8.7 Hz, 2H), 7.10 (m, 3H), 5.38 (s, 2H), 4.46 (s, 2H), 4.07 (quint, J=6.2 Hz, 1H), 3.29 (m, 4H), 2.59 (s, 3H), 1.45 (m, 1H), 1.05 (m, 2H), 0.78 (m, 9H).

REFERENCE EXAMPLE 20

N-(4-Aminobenzyl)-N-[(S)-1-isobutyl-2-ethoxyethyl]-4-(1H-2-methylimidazo[4,5-c]pyridylmethyl)phenylsulfonamide Following the procedure described in reference example 16, but using the compound obtained in reference example 19, the title compound was obtained as a white solid (46%).

mp: 67°–72° C.($C_{29}H_{37}N_5O_3S.0.5H_2O$);

$^1$H NMR (80 MHz, $CDCl_3$) δ (TMS): 9.04 (s, 1H), 8.37 (d, J=5.5 Hz, 1H), 7.75 (d, J=8.7 Hz, 2H), 7.10 (m, 5H), 6.47 (d, J=8.7 Hz, 2H), 5.35 (s, 2H), 4.22 (dd, J=16, 19 Hz, 2H), 4.05 (m, 1H), 3.16 (m, 6H), 2.59 (s, 3H), 1.45 (m, 1H), 1.10 (m, 2H), 0.90 (t, J=7.0 Hz, 3H), 0.77 (d, J=6.1 Hz, 3H), 0.69 (d, J=6.1 Hz, 3H).

EXAMPLE 1

1-[[1-[3-[4-(4-Hydroxy-3-carboxyphenylazo)phenyl]-3-methylbutanoyl]-4-piperidyl]methyl]-1H-2-methylimidazo[4,5-c]pyridine

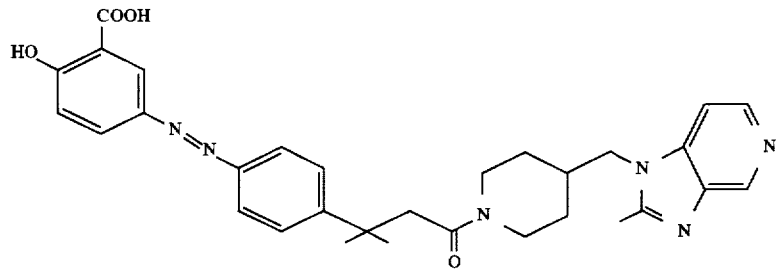

In a 25 mL flask was placed 0.92 g (2.2 mmol) of the product obtained in reference example 8. The flask was then cooled with an ice bath and a solution of fuming HCl (0.9 mL) in water (11 mL) was added. Keeping the flask in the ice bath, a solution of $NaNO_2$ (0.21 g, 3 mmol) in water (1.6 mL) was added dropwise and the mixture was stirred for 30 min. In a beaker was placed 0.33 g (2.3 mmol) of salicylic acid and a solution consisting of 6 mL of 2N NaOH and 1.5 mL of water was added. To this solution, cooled to 18° C, was added dropwise the diazonium salt, while keeping it cold. The colour of the solution gradually changed to deep red-orange and towards the end of the reaction an abundant orange-yellow solid precipitated. Towards the end of the addition of the diazonium salt solution, pH was controlled so that it remained basic until the end of the addition and finally it was brought to pH=3. Extraction with $CHCl_3$ and removal of the solvent afforded a crude product which was purified by chromatography on silica gel ($CHCl_3$:MeOH 20%) to give 0.6 g of an orange solid (55%).

mp: 185°–190° C.($C_{31}H_{34}N_6O_4.H_2O$);

$^1$H NMR (80 MHz, $CDCl_3$+$CD_3OD$) δ (TMS): 8.88 (s, 1H), 8.48 (m, 2H), 7.95 (m, 3H), 7.48 (m, 4H), 7.00 (d, J=8.9 Hz, 1H), 4.59 (m, 1H), 4.08 (m, 1H), 3.82 (d, J=7.1 Hz, 2H), 3.55 (m, 1H), 2.57 (s, 3H), 3–0.5 (complex signal, 9H), 1.61 (s, J=3H), 1.56 (s, 3H).

EXAMPLE 2 trans -1-[[1-[3-[4-(4-Hydroxy-3-carboxyphenylazo)phenyl]-3-phenylpropenoyl]-4-piperidyl]methyl]-1H-2-methylimidazo[4,5-c]pyridine

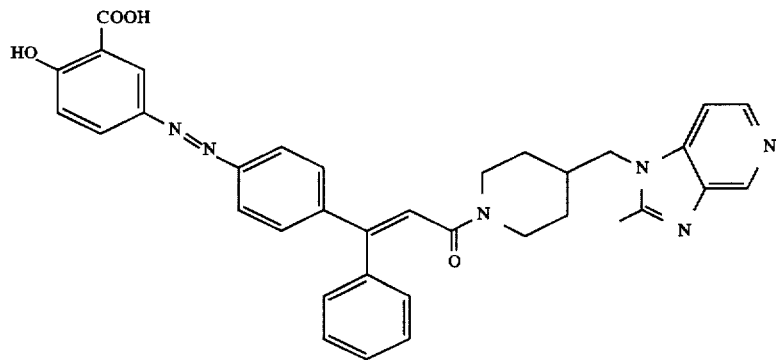

Following the procedure described in example 1, but starting from the compound obtained in reference example 11b, the title compound was obtained as an orange solid (44%).

mp: 228°–232 ° C.($C_{35}H_{32}N_6O_4.4H_2O$)

$^1$H NMR (80 MHz, $CDCl_3$+$CD_3OD$) δ (TMS): 8.93 (s, 1H), 8.45 (m, 2H), 7.92 (m, 3H), 7.40 (m, 9H), 7.30 (d, J=8.9 Hz, 1H), 6.39 (s,1H), 4.65 (m, 1H), 4.28 (m, 1H 3.94 (m, 3H), 2.61 (s, 3H), 3–0.5 (complex signal, 7H).

EXAMPLE 3 cis-1[[1-[3-[4-(4-Hydro-3-carboxyphenylazo)phenyl]-3-phenylpropenoyl]-4-piperidyl]methyl]-1H-2-methylimidazo[4,5-c]pyridine

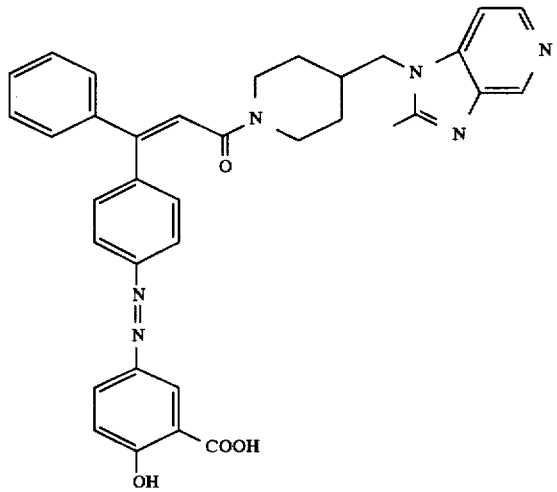

Following the procedure described in example 1, but starting from the compound obtained in reference example 11a, the title compound was obtained as an orange solid (61%).

mp: 278°–287° C. ($C_{35}H_{32}N_6O_4 \cdot H_2O$)

$^1$H NMR (80 MHz, $CDCl_3+CD_3OD$) δ (TMS): 8.86 (s, 1H), 8.47 (m, 2H), 8.01 (m, 3H), 7.37 (m, 9H), 7.00 (d, J=8.9 Hz, 1H), 6.33 (s, 1H), 4.61 (m, 1H), 4.39 (m, 1H), 3.95 (m, 1H), 3.74 (d, J=7.1 Hz, 2H), 2.54 (s, 3H), 3–0.5 (complex signal, 7H).

Following the procedure described in example 1, but starting from the compound obtained in reference example 16, the tittle compound was obtained as an orange solid (30%).

mp: 173°–180° C.($C_{36}H_{36}N_6O_8S \cdot 1.5H2O$);

$^1$H NMR (80 MHz, DMSO-$d_6$) δ (TMS): 9.10 (s, 1H), 8.34 (m, 2H), 7.74 (m, 5H), 7.35 (m, 4H), 6.91 (d, J=8.7 Hz, 2H), 5.73 (s, 2H), 5.60 (m, 2H), 5.02 (m, 1H), 4.19 (q, J=7.08 Hz, 2H), 2.59 (s, 3H), 1.91 (m, 3H), 1.21 (t, J=7.0 Hz, 3H), 0.89 (t, J=6.1 Hz, 3H), 0.82 (d, J=6.1 Hz, 3H).

EXAMPLE 4

1-[[1-[[N-[[4-(4-Hydroxy-3-carboxyphenylazo) phenyl]sulfonil]-N-phenylamino]acetyl]-4-piperidyl] methyl]-1H-2-methylimidazo[4,5-c]pyridine

EXAMPLE 6

N-[4-(4-Hydroxy-3-carboxyphenylazo)benzyl]-N-[4-(1H-2-methylimidazo[4,5-c]pyridylmethyl) phenylsulfonyl]-L-leucine ethyl ester

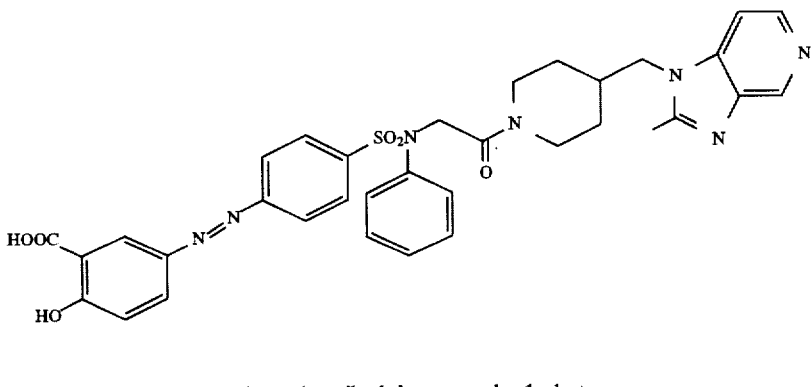

Following the procedure described in example 1, but starting from the compound obtained in reference example 14, the title compound was obtained as an orange solid (25%).

mp: 195°–200° C. ($C_{34}H_{33}N_7O_6S \cdot 2H_2O \cdot 0.5DMF$) $^1$H NMR (80MvHz, DMSO-$d_6$) δ (TMS): 9.06 (s, 1H), 8.33 (m, 2H), 7.82 (m, 7H), 7.26 (m, 5H), 6.80 (d, J=8.9 Hz, 1H), 4.14 (m, 5H), 2.88 (s, 3H), 3–1 (complex signal, 9H).

EXAMPLE 5

N-[4-(4-Hydroxy-3-carboxyphenylazo)benzoyl]-N-[4-(1H-2-methylimidazo[4,5-c]pyridylmethyl) phenylsulfonyl]-L-leucine ethyl ester

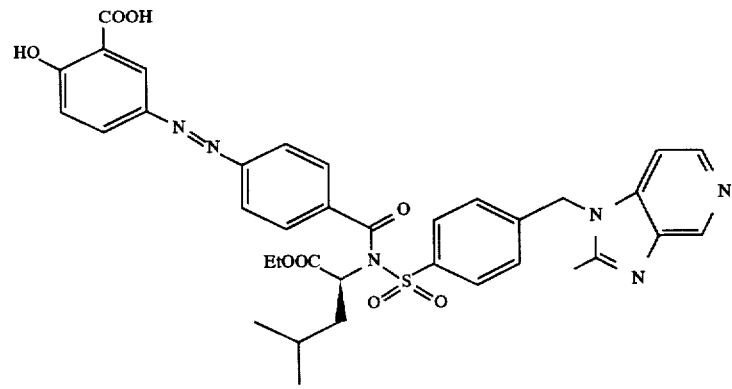

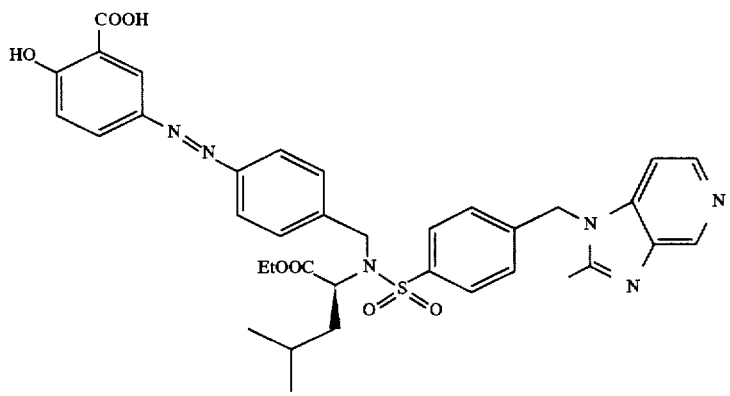

Following the procedure described in example 1, but using the compound obtained in reference example 18, the title compound was obtained as an orange solid (18%).

mp: 177°–176° C.($C_{36}H_{38}N_6O_7S \cdot 2H_2O$);

$^1$H NMR (80 MHz, CDCl$_3$+CD$_3$OD) δ (TMS): 8.97 (s, 1H), 8.53 (s, 1H), 8.37 (m, 1H), 8.00 (d, J=9.0 Hz, 1H), 7.75 (m, 4H), 7.18 (m, 6H), 5.43 (s, 2H), 4.58 (dd, J=10.7, 13 Hz, 2H), 4.52 (m, 1H), 4.06 (m, 2H), 3.89 (q, J=7.08 Hz, 2H), 2.60 (s, 3H), 1.57 (m, 3H), 1.08 (t, J=7.0 Hz, 3H), 0.95 (t, J=5.1 Hz, 3H), 0.64 (d, J=5.1 Hz, 3H).

EXAMPLE 7

N-[4-(4-Hydroxy-3-carboxyphenylazo)benzyl]-N-[(S)-1-isobutyl-2-ethoxyethyl]-4-(1H-2-methylimidazo[4,5-c]pyridylmethyl)phenylsulfonamide

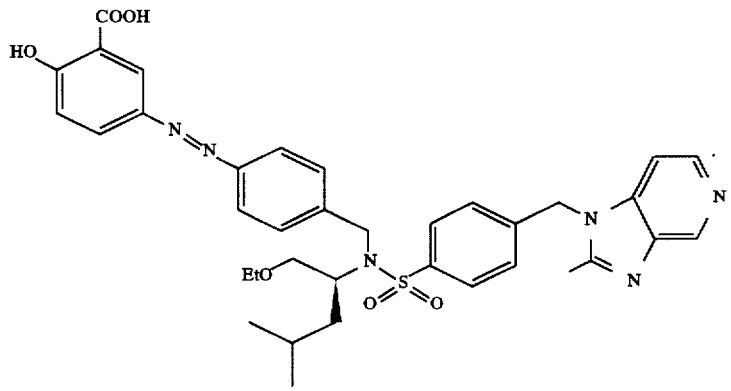

Following the procedure described in example 1, but using the compound obtained in reference example 20, the title compound was obtained as an orange solid (35%).

mp: 170°–173° C.($C_{36}H_{40}N_6O_6S \cdot H_2O$);

$^1$H NMR (80 MHz, CDCl$_3$+CD$_3$OD) δ (TMS): 8.95 (s, 1H), 8.51 (s, 1H), 8.37 (m, 1H), 8.00 (d, J=9.0 Hz, 1H), 7.66 (m, 4H), 7.33 (m, 3H), 7.00 (d, J=8.5 Hz, 3H), 5.35 (s, 2H), 4.42 (s, 2H), 4.22 (m, 1H), 3.33 (m, 5H), 2.57 (s, 3H), 1.55 (m, 1H), 1.28 (m, 3H), 0.95 (t, J=7.1 Hz, 3H), 0.85 (t, J=6.0 Hz, 3H), 0.77 (d, J=6.0 Hz, 3H).

We claim:

1. A compound of formula I:

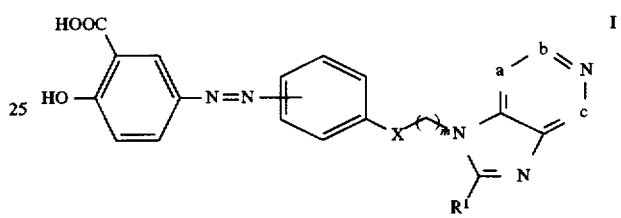

wherein:

the 4-hydroxy-3-carboxyphenylazo moiety may be at the 3- or 4-position of the benzene ring;

m represents 1 or 2;

R$^1$ represents C$_{1-4}$ alkyl or C$_{3-7}$ cycloalkyl;

a, b and c represent CR$^2$, wherein each R$^2$ independently represents hydrogen or C$_{1-4}$ alkyl;

X represents a group of formula (i) or (ii):

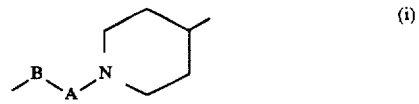

(i)

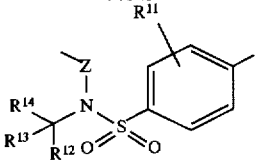

wherein these groups are bound to the phenyl ring in formula I via B and Z, respectively;

A represents —CO—, —SO$_2$—, —NHCO— or —OCO—,

B represents a group of formula (iii), and when A represents —CO— or —SO$_2$—, B may also represent a group of formula (iv), (v), (vi) or (vii);

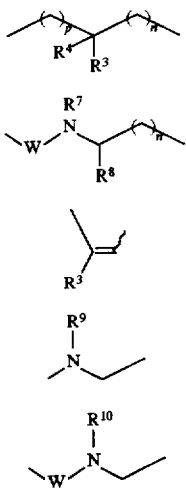

n represents 0, 1, 2 or 3;

p represents 0 or 1;

R$^3$ represents hydrogen, C$_{1-4}$ alkyl, C$_{1-4}$ haloalkyl, C$_{3-7}$ cycloalkyl, C$_{1-4}$ alkoxy-C$_{1-4}$ alkyl or aryl;

R$^4$ represents hydrogen, C$_{1-4}$ alkyl, —COOR$^5$ or —CONR$^5$R$^6$, and when A represents —CO— or —SO$_2$—, then R$^4$ can also represent —NR$^5$R$^6$, —NR$^7$C(=O)OR$^5$, —NR$^7$C(=O)R$^5$, —NR$^7$C(=O)NR$^5$R$^6$ or —NR$^7$SO$_2$R$^5$;

or R$^3$ and R$^4$ together form a C$_{2-6}$ polymethylene chain;

R$^5$ represents C$_{1-4}$ alkyl, aryl or aryl-C$_{1-4}$ alkyl;

R$^6$ and R$^7$ independently represent hydrogen or C$_{1-4}$ alkyl;

W represents —OC(=O)—, —C(=O)—, —NR$^6$C(=O)— or —SO$_2$—;

R$^8$ represents aryl;

R$^9$ represents C$_{1-4}$ alkyl, C$_{3-7}$ cycloalkyl, -C(=O)OR$^5$, —C(=O)R$^5$, —C(=O)NR$^5$R$^6$, or —SO$_2$R$^5$;

R$^{10}$ represents C$_{1-4}$ alkyl, C$_{3-7}$ cycloalkyl, aryl, or aryl-C$_{1-4}$ alkyl;

Z represents —(CH2)$_q$CO— or —(CH$_2$)$_r$—;

q represents 0, 1 or 2;

r represents 1 or 2;

R$^{11}$ represents hydrogen or halogen;

R$^{12}$ and R$^{13}$ independently represent hydrogen, C$_{1-6}$ alkyl, C$_{3-7}$ cycloalkyl or C$_{3-7}$ cycloalkyl-C$_{1-6}$ alkyl;

or R$^{12}$ and R$^{13}$ together form a C$_{2-6}$ polymethylene chain;

R$^{14}$ represents —COR$^{15}$, —COOH, —COOR$^{15}$, —CONR$^{16}$R$^{17}$, —C$_{1-6}$ alkyl-OR$^{15}$, —C$_{1-6}$ alkyl-OC(=O)R$^{15}$ or —C$_{1-6}$ alkyl-OC(=O)NR$^{16}$R$^{17}$;

R$^{15}$ represents C$_{1-6}$ alkyl, C$_{2-6}$ alkenyl, C$_{2-6}$ alkynyl, C$_{3-7}$ cycloalkyl or C$_{1-6}$ haloalkyl;

R$^{16}$ and R$^{17}$ independently represent hydrogen or any of the meanings disclosed for R$^{15}$;

aryl, whenever appearing in the above definitions, represents phenyl or phenyl substituted with 1, 2, 3 or 4 groups independently selected from halogen, C$_{1-4}$ alkyl, C$_{1-4}$ alkoxy, hydroxy, C$_{1-4}$ haloalkyl, C$_{1-4}$ haloalkoxy, C$_{1-4}$ alkylcarbonyl, C$_{1-4}$ alkylcarbonyloxy, C$_{1-4}$ alkoxycarbonyl, C$_{1-4}$ alkylsulfonyl, C$_{1-4}$ alkylsulfinyl, C$_{1-4}$ alkylthio, or C$_{1-4}$ alkylcarbonylamino;

and the salts and solvates thereof.

2. A compound as claimed in claim 1 wherein X represents a group of formula (i).

3. A compound as claimed in claim 2 wherein A represents —CO—.

4. A compound as claimed in claim 3 wherein B represents a group of formula (iii), (v) or (vii).

5. A compound as claimed in claim 4 wherein B represents a group of formula (iii) and p represents 0.

6. A compound as claimed in claim 4 wherein B represents a group of formula (v) and R$^3$ represents C$_{1-4}$ alkyl, C$_{1-4}$ haloalkyl, C$_{3-7}$ cycloalkyl, C$_{1-4}$ alkoxy-C$_{1-4}$ alkyl or aryl.

7. A compound as claimed in claim 4 wherein B represents a group of formula (vii).

8. A compound as claimed in claim 1 wherein X represents a group of formula (ii).

9. A compound as claimed in claim 8 wherein m represents 1.

10. A compound as claimed in claim 9 wherein R$^{12}$ represents C$_{1-6}$ alkyl, C$_{3-7}$ cycloalkyl or C$_{3-7}$ cycloalkyl-C$_{1-6}$ alkyl; and R$^{13}$ represents hydrogen.

11. A compound as claimed in claim 10 wherein R$^{14}$ represents —COR$^{15}$, —COOR$^{15}$ or —C$_{16}$ alkyl-OR$^{15}$.

12. A compound as claimed in claim 11 wherein R$^{15}$ represents C$_{1-6}$ alkyl.

13. A compound as claimed in claim 1 selected from:

(a) 1-[[1-[3-[4-(4-hydroxy-3-carboxyphenylazo)phenyl]-3-methyl-butanoyl]-4-piperidyl]methyl]-1H-2-methylimidazo[4,5-c]pyridine;

(b) trans-1-[[1-[3-[4-(4-hydroxy-3-carboxyphenylazo)phenyl]-3-phenyl-propenoyl]-4-piperidyl]methyl]-1H-2-methylimidazo[4,5-c]pyridine;

(c) cis-1- [[1- [3- [4- (4-hydroxy-3-carboxyphenylazo)phenyl]-3-phenyl-propenoyl]-4-piperidyl]methyl]-1H-2-methylimidazo[4,5-c]pyridine;

(d) 1-[[1-[[N-[[4-(4-hydroxy-3-carboxyphenylazo)phenyl]sulfonyl]-N-phenylamino]acetyl]-4-piperidyl]methyl]-1H-2-methylimidazo[4,5-c]pyridine;

(e) N-[4-(4-hydroxy-3-carboxyphenylazo)benzoyl]-N-[4-(1H-2-methylimidazo[4,5-c]pyridylmethyl)phenylsulfonyl]-L-leucine ethyl ester;

(f) N-[4-(4-hydroxy-3-carboxyphenylazo)benzyl]-N-[4-(1H-2-methylimidazo[4,5-c]pyridylmethyl)phenylsulfonyl]-L-leucine ethyl ester;

(g) N-[4-(4-hydroxy-3-carboxyphenylazo)benzyl]-N-[(S)-1-isobutyl-2-ethoxyethyl]-4-(1H-2-methylimidazo[4,5-c]pyridylmethyl)phenylsulfonamide;

14. A process for preparing a compound of formula I as defined in claim 1, which comprises:

(a) converting an amine of formula II

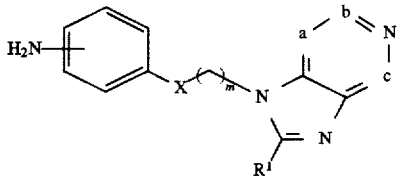

wherein the amino group may be at the 3- or 4-position of the benzene ring and a, b, c, m, $R^1$ and X are as defined in claim 1, into the corresponding diazonium salt, and then allowing this to react with salicylic acid; or (b) reacting an amine of formula II with 5-nitrososalicylic acid; or (c) reacting a nitroso derivative of formula

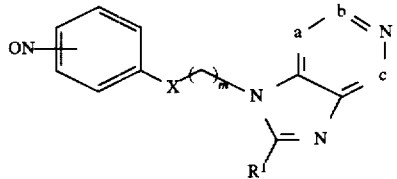

wherein the NO group can be at the 3- or 4-position of the benzene ring and a, b, c, m, $R^1$ and X are as defined in claim 1, with 5-aminosalicylic acid; and (d) optionally, after steps (a), (b) or (c), reacting a compound of formula I with an acid or a base to give the corresponding salt.

15. A pharmaceutical composition which comprises an effective amount of a compound of formula I as claimed in claim 1 or a pharmaceutically acceptable salt or solvate thereof in admixture with one or more pharmaceutically acceptable excipients.

16. A method for the prevention or treatment of inflammatory bowel disease in an animal or human, said method comprising administering an effective amount to prevent or treat inflammatory bowel disease of the compound of formula I according to claim 1 to an animal or human in need of such prevention or treatment.

* * * * *